US009792407B2

(12) United States Patent
Ootsuki et al.

(10) Patent No.: US 9,792,407 B2
(45) Date of Patent: *Oct. 17, 2017

(54) SERVER DEVICE, IMAGE TRANSMISSION METHOD, TERMINAL DEVICE, IMAGE RECEPTION METHOD, PROGRAM, AND IMAGE PROCESSING SYSTEM

(71) Applicant: Sony Corporation, Tokyo (JP)

(72) Inventors: Tomoyuki Ootsuki, Kanagawa (JP); Kazuki Aisaka, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/191,507

(22) Filed: Jun. 23, 2016

(65) Prior Publication Data
US 2017/0027442 A1    Feb. 2, 2017

Related U.S. Application Data

(63) Continuation of application No. 14/350,232, filed as application No. PCT/JP2012/006619 on Oct. 16, 2012, now Pat. No. 9,400,869.

(30) Foreign Application Priority Data

Oct. 19, 2011 (JP) ................. 2011-229847

(51) Int. Cl.
G06F 19/00   (2011.01)
G06F 17/30   (2006.01)
(Continued)

(52) U.S. Cl.
CPC .............. *G06F 19/321* (2013.01); *A61B 3/12* (2013.01); *G06F 17/30265* (2013.01);
(Continued)

(58) Field of Classification Search
CPC ......... G06F 17/30265; G06F 17/30268; G06F 17/30274; G06F 19/321; G06T 5/00–5/50
See application file for complete search history.

(56) References Cited

U.S. PATENT DOCUMENTS 6,711,622 B1 * 3/2004 Fuller ............... H04L 29/06027
                                                    709/231
8,467,580 B2   6/2013 Suito et al.
(Continued)

FOREIGN PATENT DOCUMENTS

EP   1 185 106 A1   3/2002
JP   2005-044004 A  2/2005
WO   WO 02/25588 A2 3/2002

OTHER PUBLICATIONS

No Author Listed, Karl Storz-Endoskope, Karl Storz Aida® compact NEO Instruction Manual,© 2011KARL Storz GmbH & Co. KG, 152 pages.

Primary Examiner — Paul Berardesca
(74) Attorney, Agent, or Firm — Wolf, Greenfield & Sacks, P.C.

(57) ABSTRACT

In some embodiments, methods and apparatus are provided for transmitting, via at least one network, a request to another apparatus for still image data generated from moving image data, the request comprising at least one criterion, and receiving still image data generated from moving image data matching the at least one criterion in the request. In further embodiments, methods and apparatus are provided for receiving the request via at least one network, using the at least one criterion in the request to obtain still image data generated from moving image data, and responding to the request by transmitting the obtained still image data.

22 Claims, 17 Drawing Sheets

(51) Int. Cl.
  *H04L 29/08* (2006.01)
  *G06T 5/00* (2006.01)
  *H04N 5/235* (2006.01)
  *H04N 5/21* (2006.01)
  *H04N 5/232* (2006.01)
  *A61B 3/12* (2006.01)
  *H04N 1/00* (2006.01)
  *A61B 3/00* (2006.01)

(52) U.S. Cl.
  CPC .............. *G06T 5/003* (2013.01); *H04L 67/12* (2013.01); *H04N 5/21* (2013.01); *H04N 5/2355* (2013.01); *H04N 5/23232* (2013.01); *A61B 3/0025* (2013.01); *H04N 1/00413* (2013.01)

(56) References Cited

U.S. PATENT DOCUMENTS

| | | |
|---|---|---|
| 8,537,212 B2 | 9/2013 | Kunihiro et al. |
| 9,400,869 B2 | 7/2016 | Ootsuki et al. |
| 2003/0013951 A1* | 1/2003 | Stefanescu ........ G06F 17/30256 600/407 |
| 2007/0236734 A1* | 10/2007 | Okamoto ........... G03G 15/5004 358/1.16 |
| 2008/0166021 A1 | 7/2008 | Suito et al. |
| 2011/0103659 A1 | 5/2011 | Choi |
| 2011/0234828 A1 | 9/2011 | Kunihiro et al. |
| 2014/0232899 A1 | 8/2014 | Ootsuki et al. |
| 2016/0048230 A1 | 2/2016 | Shimoda |

\* cited by examiner

[Fig. 2]

[Fig. 5]
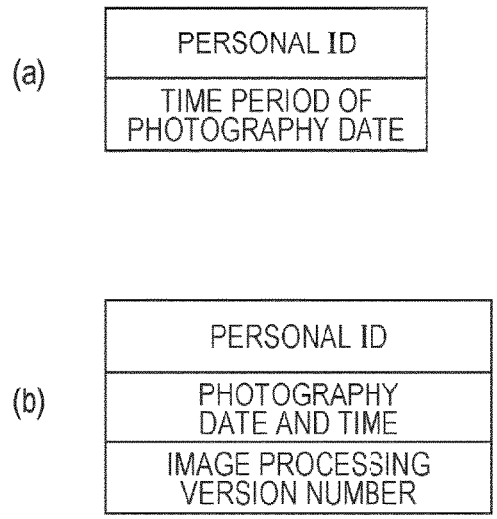
[Fig. 6]
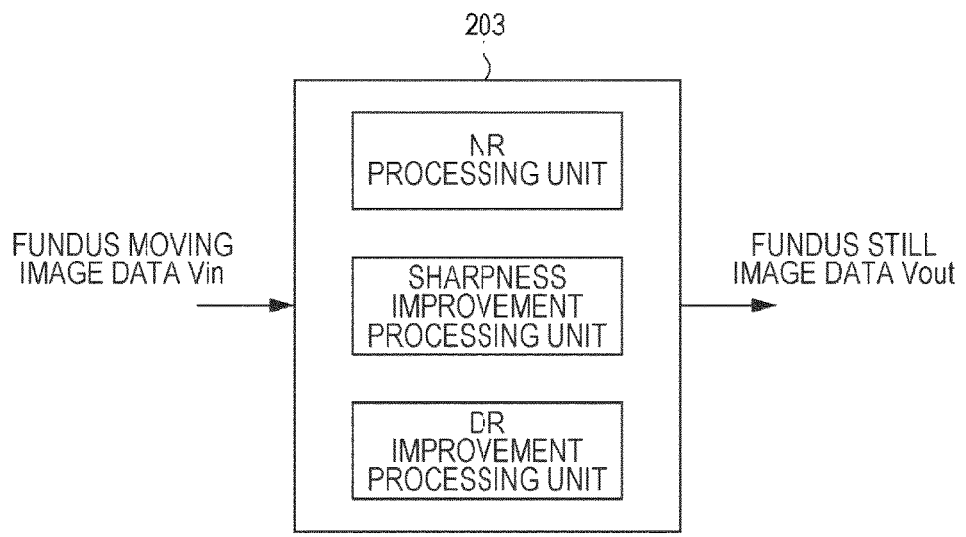

[Fig. 7]
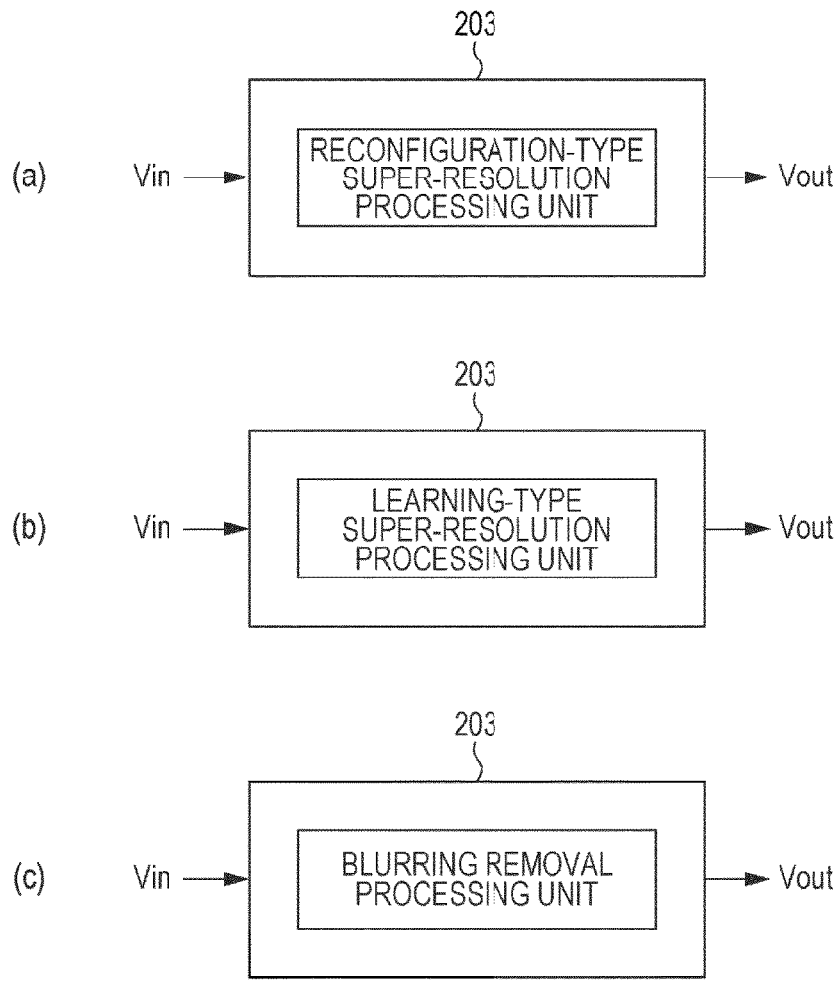
[Fig. 8]
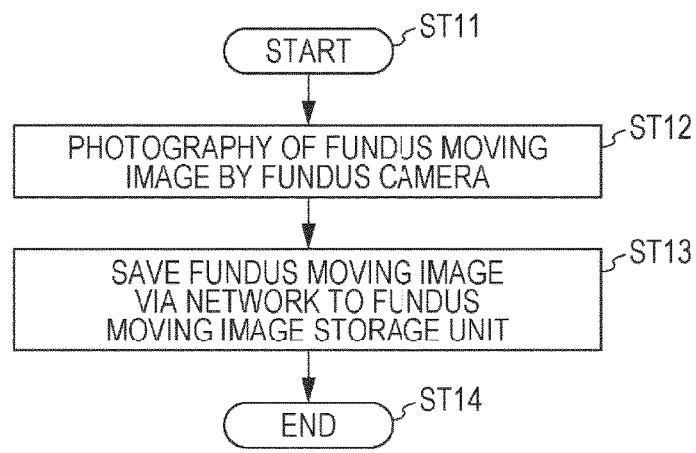

[Fig. 9]
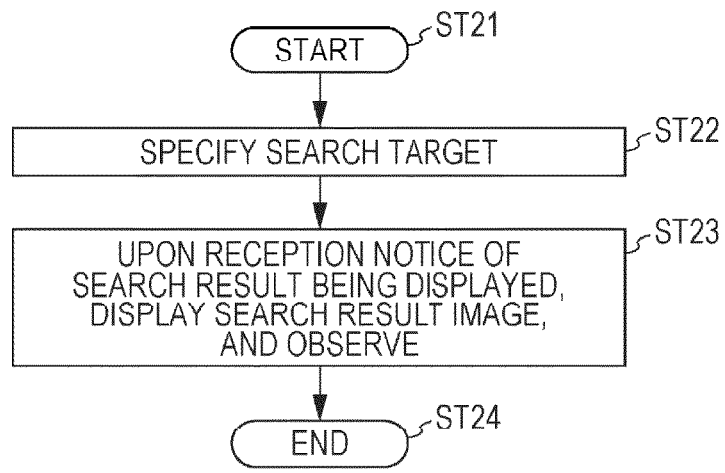
[Fig. 10]
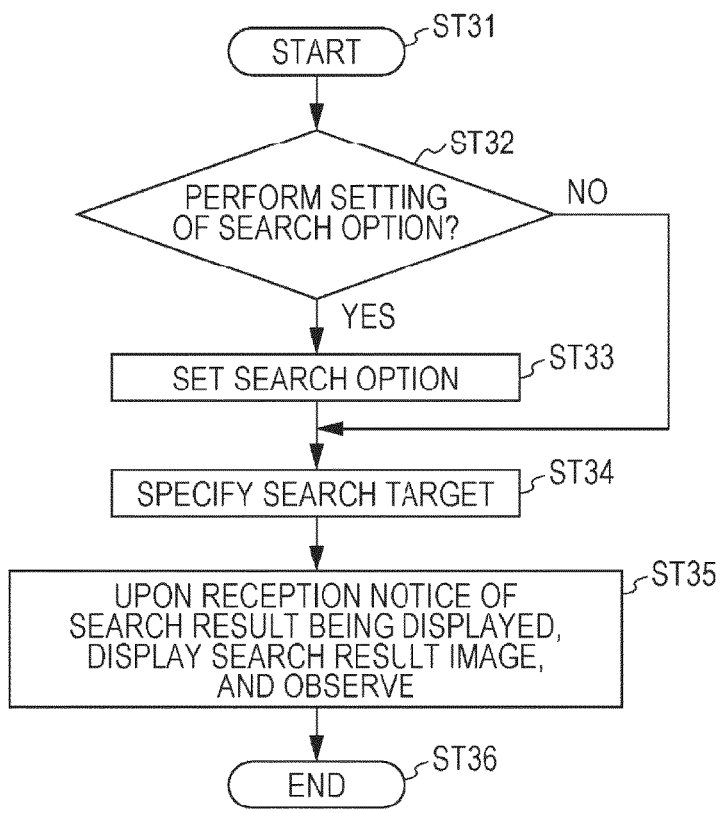

[Fig. 11]
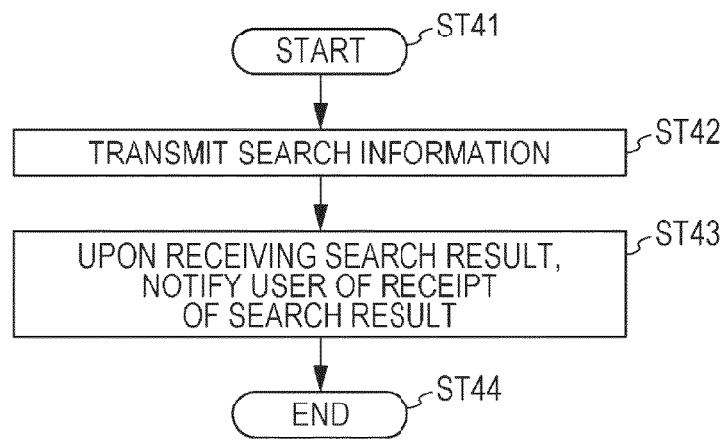

[Fig. 12]
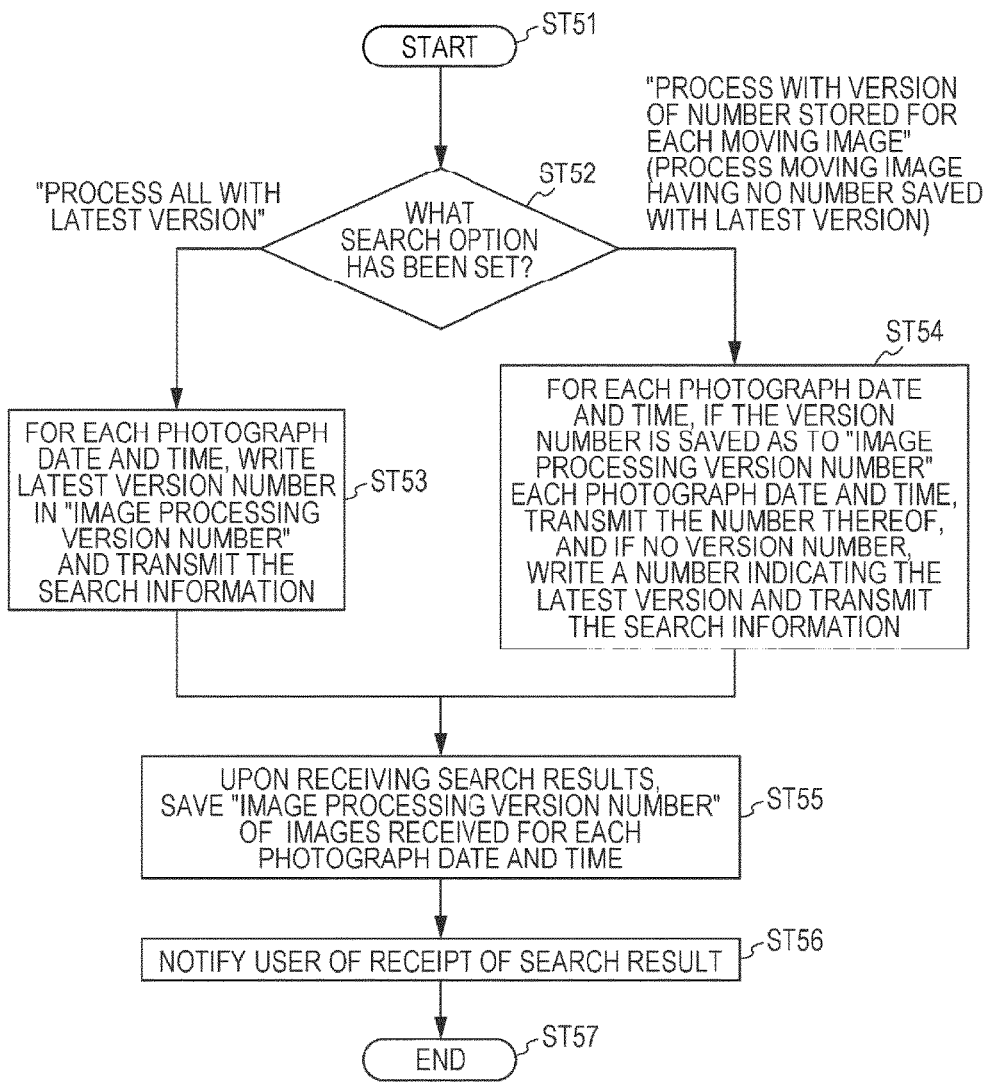

[Fig. 13]
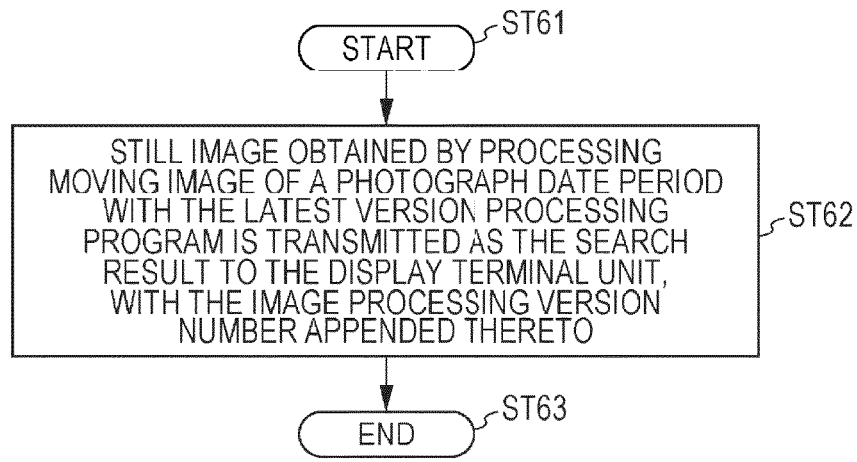
[Fig. 14]
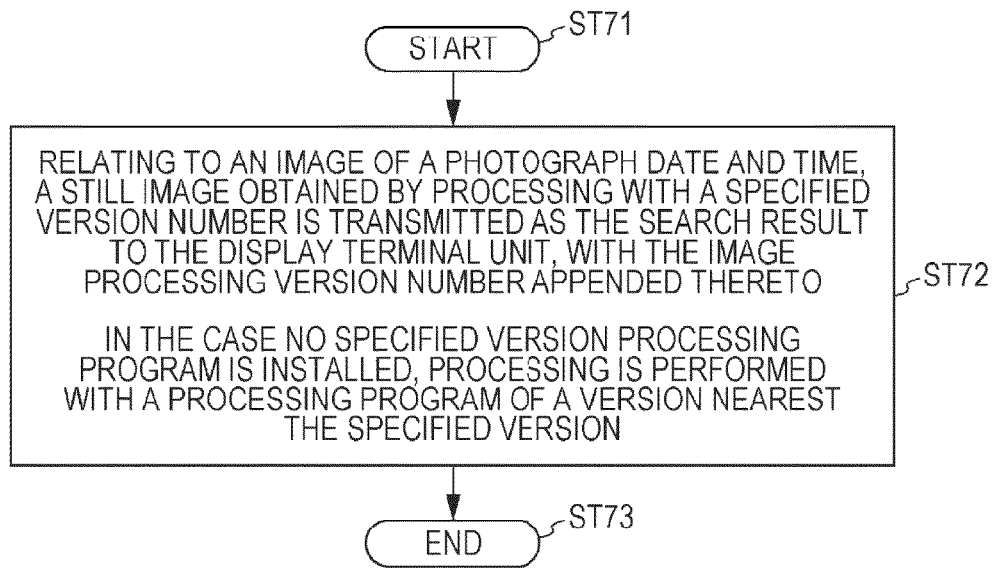

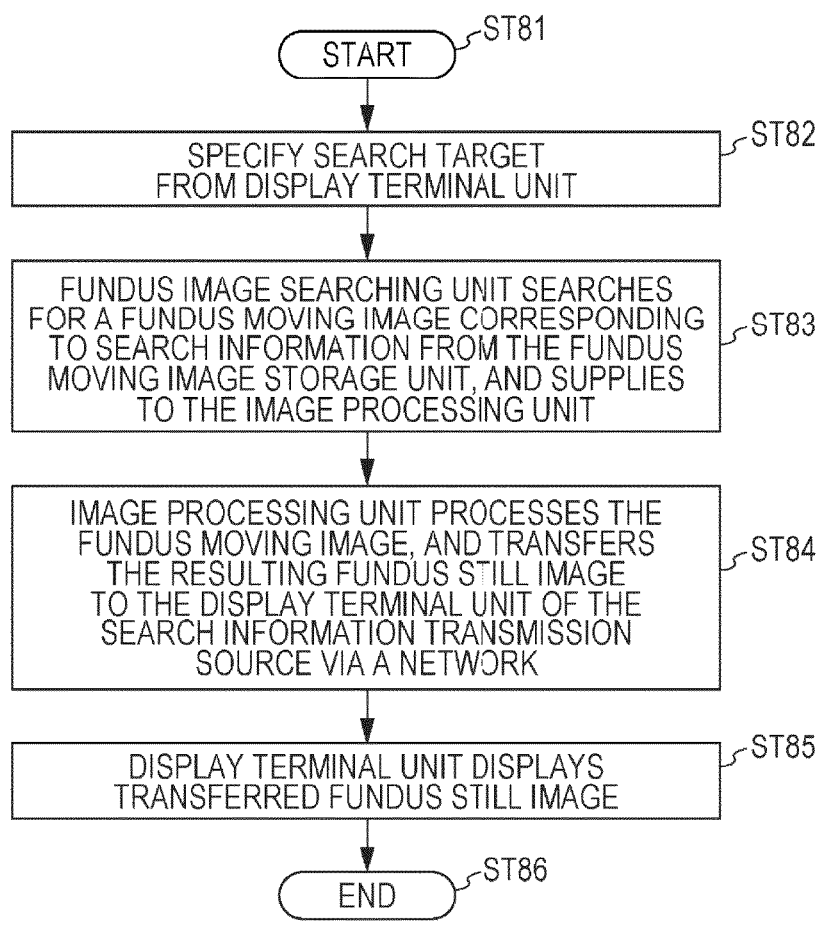
[Fig. 15]

[Fig. 17]
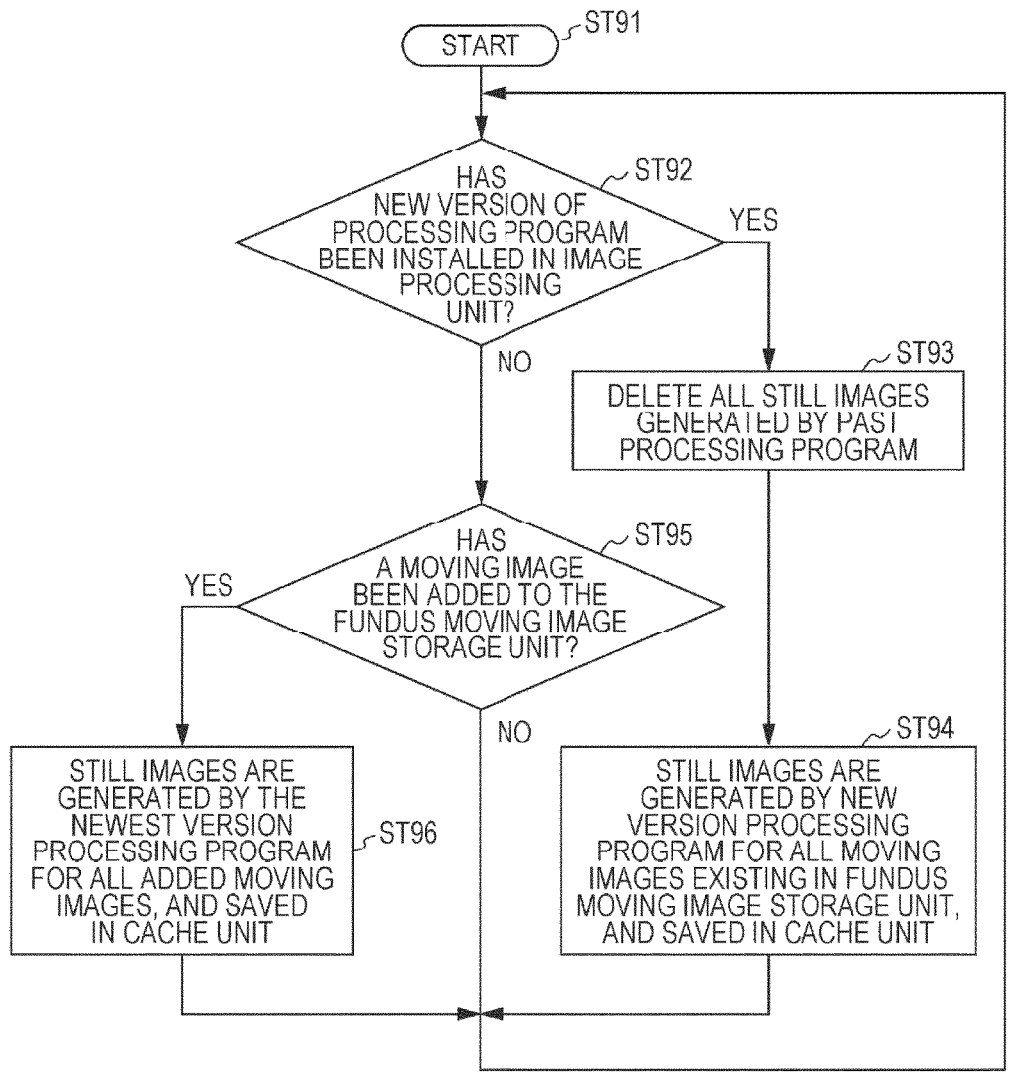

[Fig. 18]
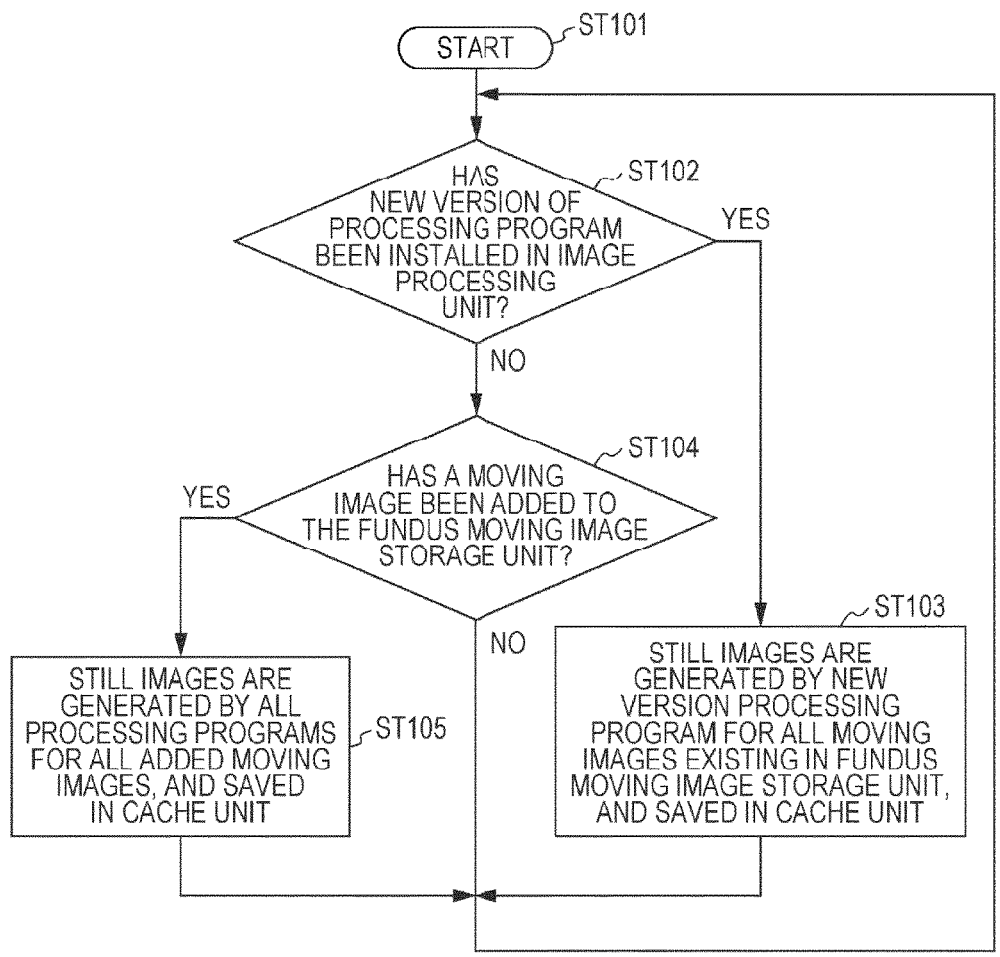

[Fig. 19]
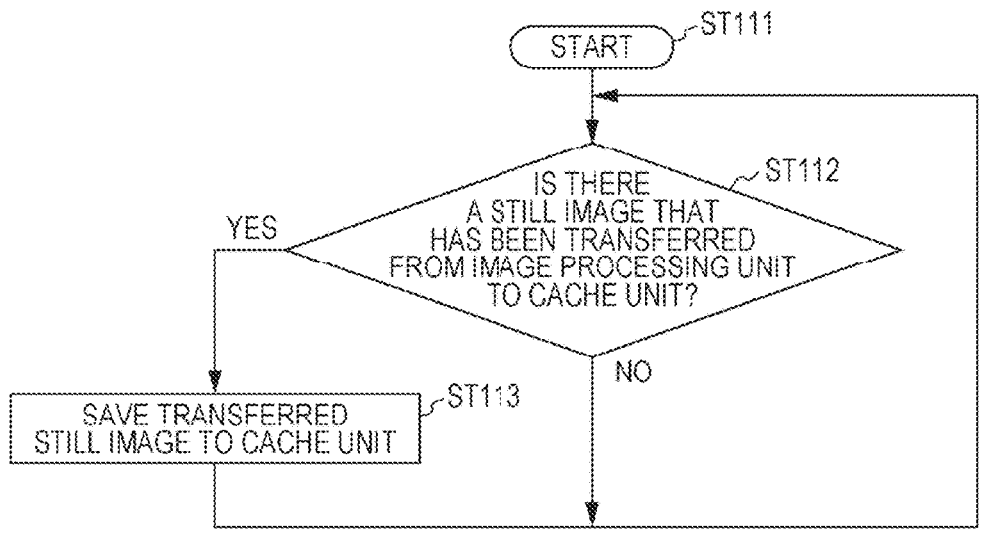
[Fig. 20]
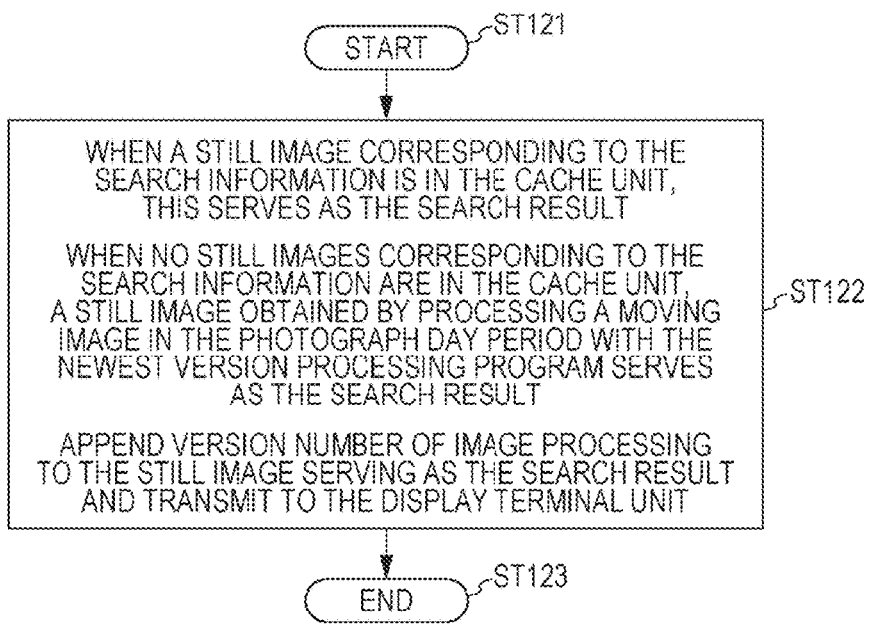

[Fig. 21]
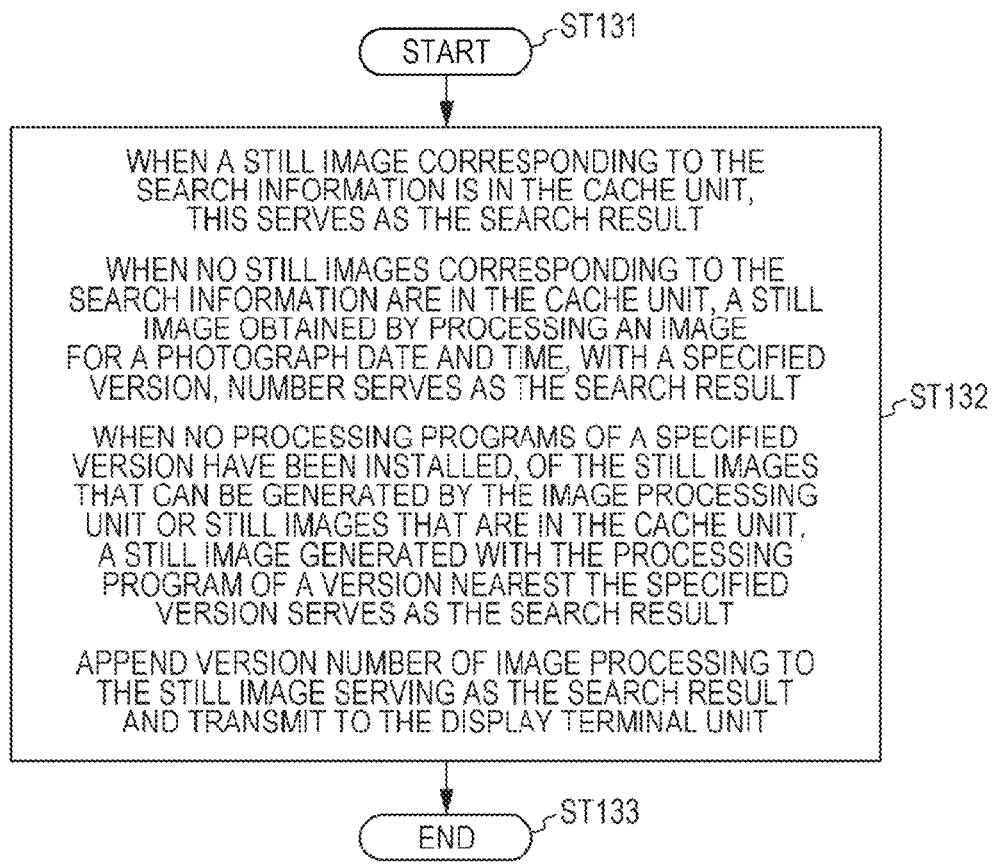

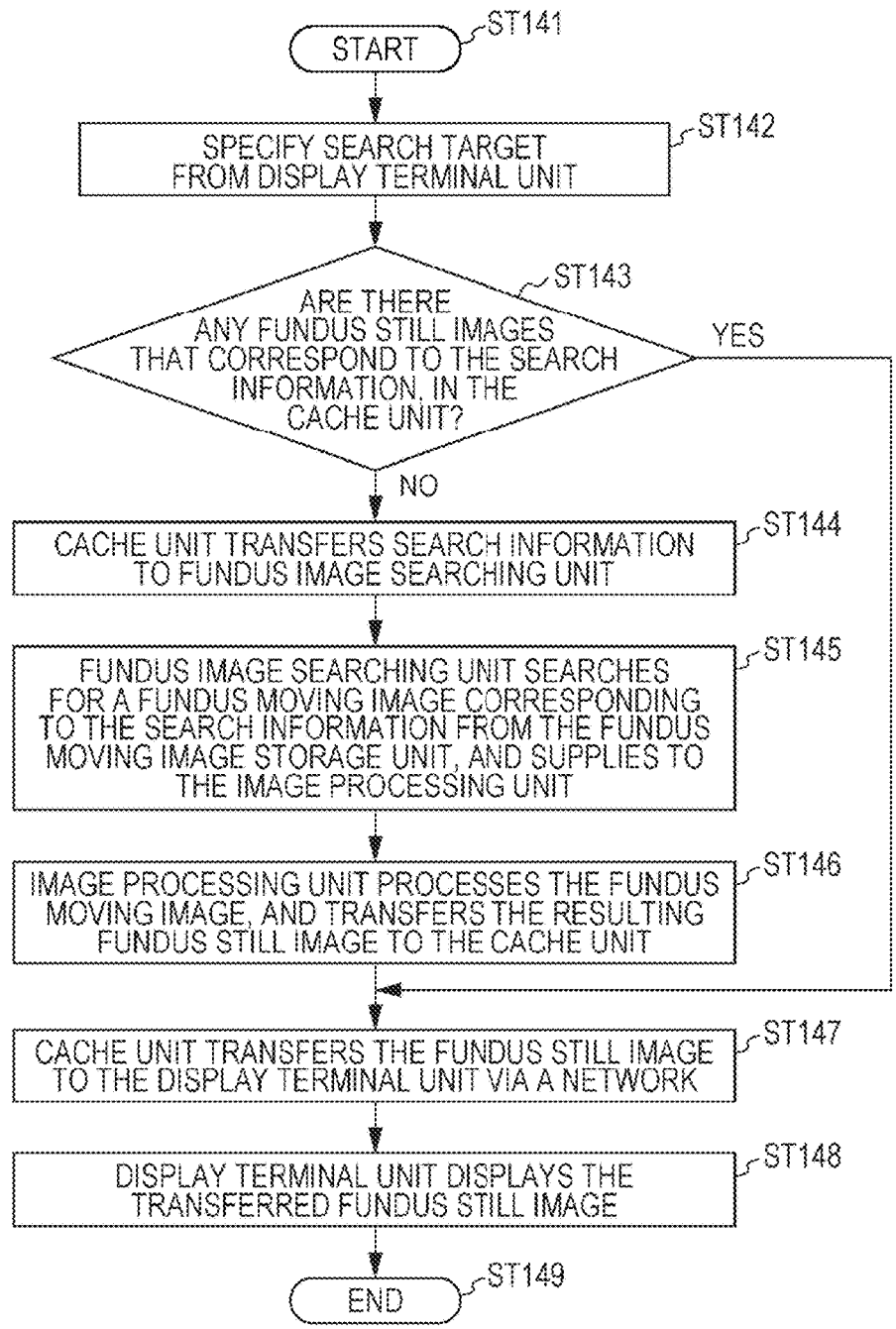

SERVER DEVICE, IMAGE TRANSMISSION METHOD, TERMINAL DEVICE, IMAGE RECEPTION METHOD, PROGRAM, AND IMAGE PROCESSING SYSTEM

CROSS REFERENCES TO RELATED APPLICATIONS

This is a continuation application of U.S. patent application Ser. No. 14/350,232, filed on Apr. 7, 2014, which is a national stage of International Application No. PCT/JP2012/006619, filed on Oct. 16, 2012, which in turn claims priority from Japanese Application No. 2011-229847, filed on Oct. 19, 2011, the entire contents of which are incorporated herein by reference.

TECHNICAL FIELD

The present invention relates to a server device, image transmission method, terminal device, image reception method, program, and image processing system, and particularly relates to a server device and so forth that handles high quality still images generated from a moving image by image processing.

BACKGROUND ART

In general, a so-called funduscopy, by which observation of the fundus such as the retina and optic disc and so forth within the eye, via the pupil, is performed. A funduscopy is performed using a specialized device such as a funduscope or fundus camera. For example, an observer photographs the fundus within the eye of a subject, which is the observation target, with a fundus camera, displays the obtained fundus image on a monitor or the like, and performs observation.

Also, the image data of the fundus image thus photographed and obtained with a fundus camera may be saved in storage such as an HDD (Hard Disk Drive), and used for discussion thereafter or explanation to a patient and so forth. For example, PTL 1 discloses that, as image data of a medical image, not only still image data, but moving image data may be saved. For example, in order to show endoscopy images to a patient, description is difficult with just still images, so display of moving images is also enabled.

CITATION LIST

Patent Literature

PTL 1: JP 2005-044004A

SUMMARY OF INVENTION

Technical Problem

A fundus camera normally photographs still images. In order to more accurately perform observation of a fundus image, the fundus image has to have a higher image quality. In order to improve the image quality of the fundus image, photographing a moving image with a fundus camera, performing image processing as to this moving image to generate still images, thereby improving the image quality, can be conceived. In this case, if the medical institutions individually perform image processing, in the event that a new processing algorithm has been developed, the hardware or software (processing program) has to be individually updated, resulting in a high cost for updates.

An object of the present technology is to enable obtaining still images of higher quality fundus images and the like in medical institutions or the like at a low cost, for example.

Solution to Problem

According to some embodiments of the present disclosure, an apparatus is provided, comprising at least one processor programmed to: receive, via at least one network, a request from another apparatus for still image data generated from moving image data, the request comprising at least one criterion; use the at least one criterion in the request to obtain still image data generated from moving image data; and respond to the request by transmitting the obtained still image data. According to some further embodiments of the present disclosure, a server device is provided, including an image processing unit to generate still image data from moving image data stored in a storage unit, wherein a processing program can be automatically updated or added thereto;

a search information receiving unit to receive search information transmitted from a terminal device;

and an image transmission unit to transmit, to the terminal device, still image data generated by processing predetermined moving image data using a predetermined processing program, such still image data corresponding to search information received by the search information receiving unit.

According to some embodiments of the present technology, still image data may be generated from moving image data stored in a storage unit by an image processing unit. The image processing unit can automatically modify or add a processing program. For example, the modification or addition of a processing program is performed in the event that a new processing algorithm is developed, i.e. in the event that a version updated to the processing program becomes available. For example, with the image processing unit, one or more of NR (noise reduction), sharpness improvement, and DR (dynamic range) improvement is executed, and high quality still image data is generated.

The moving image data stored in the storage unit is transmitted from a terminal device that is the same or different from the terminal device, via a network, for example. However, the moving image data may also be provided by a removable memory or the like. Also, for example, the moving image data is moving image data of medical images, but should not be restricted to this.

As a sharpness improvement method, a reconfiguration-type super-resolution processing, learning-type super-resolution processing, or blurring removal processing, for example, may be used. The reconfiguration-type super-resolution processing is processing to layer the image data of multiple frames, based on the moving image data, thereby generating high quality still image data wherein the dynamic range has been extended. Also, the learning-type super-resolution processing is processing to perform super-resolution processing using a dictionary that has been generated through learning, and generates high quality still image data. The blurring removal processing is processing to cancel blurring in an image and generate a sharp image, using blind deconvolution, for example.

According to some embodiments of the present disclosure, search information transmitted from a terminal device may be received by a search information receiving unit. The still image data generated by processing predetermined moving image data with a predetermined program, corresponding to the search information, is transmitted to the terminal device by the image transmitting unit. For example, search information includes first information that identifies moving image data and second information that identities a processing program to generate still image data from the moving image data, and the still image data that has been generated by processing the moving image data identified by a first information and by a processing program identified by the second information, may be transmitted to the terminal device.

Thus, according to some embodiments of the present technology, the image processing unit can automatically modify or add a processing program. Also, still image data generated by processing predetermined moving image data corresponding to the search information transmitted from the terminal device with a predetermined processing program is transmitted to the terminal device. Therefore, it goes without saying that the display terminal units can obtain high quality still image data by the newest processing algorithm at a low cost, rather than performing image processing by themselves. Further more, because medical images tend to contain a large amount of information (e.g., stored in large files), processing of such images may be computationally intensive. In various disclosed embodiments, the terminal device can advantageously obtain high quality still image data without having to perform intensive computations locally. Also, the display terminal units can obtain still images with not only the newest version of the processing program, but with an optional version of a processing program, and can be favorably applied to past observations such as medical images or the like. In various embodiments, a specific version of the processing program may be selected, which may or may not be the newest version. For example, if a specific version was used to process past observations from a patient, it may be desirable to use the same version to process present observations of the patient to facilitate accurate comparison between the past and present observations.

Note that according to some embodiments of the present technology, a cache unit is further provided that holds the still image data generated by the image processing unit, for example, and in the case that still image data corresponding to the search information from the terminal device is held in the cache unit, the image transmitting unit may retrieve the still image data from the cache unit and transmit this to the terminal device. By such a cache unit being provided, the still image data existing already in the cache unit does not have to be generated by the image processing unit, and the still image data corresponding to the search information can be efficiently transmitted to the terminal device.

For example, still image data generated by processing the moving image data stored in the storage unit by the newest version of the processing program in the image processing unit may conceivably be held in the cache unit. Also, for example, still image data generated by processing moving image data stored in the storage unit by all of the processing programs in the image processing unit may conceivably be held in the cache unit. Also, for example, still image data corresponding to the search information from the terminal device that has been transmitted to the terminal device in the past by the image transmitting unit may conceivably be held in the cache unit.

According to some further embodiments of the present disclosure, an apparatus is provided, comprising at least one processor programmed to: transmit, via at least one network, a request to another apparatus for still image data generated from moving image data, the request comprising at least one criterion; and receive still image data generated from moving image data matching the at least one criterion in the request. According to yet some further embodiments of the present disclosure, a terminal device is provided that has a search information transmitting unit to transmit, to a server device, search information including first information that identifies moving image data and second information that identifies a processing program to generate still image data from the moving image data; and an image receiving unit to receive the still image data generated by processing predetermined moving image data with a predetermined processing program, corresponding to the search information, the still image data having been transmitted from the server device.

According to some embodiments of the present technology, search information may be transmitted from the search information transmitting unit to the server device. The search information includes first information identifying moving image data and second information identifying a processing program to generate the still image data from the moving image data. Still image data generated by processing predetermined moving image data corresponding to the search information which is transmitted from the server device, with a predetermined processing program, may be received by the image receiving unit.

Thus, according to some embodiments of the present technology, the first information identifying moving image data and second information identifying a processing program to generate the still image data from the moving image data can be transmitted to the server device, and the still image data generated by processing predetermined moving image data corresponding to the search information from the server device, with a predetermined processing program, can be received. Accordingly, high quality still image data can be obtained by newest processing programs at a low cost, besides performing image processing by itself. Also, still images can be obtained, with not only the newest processing program, but with an optional processing program, and can be favorably applied to past observations such as medical images or the like.

Note that according to some embodiments of the present technology, a user interface unit may further be provided, to select whether to identify the newest processing program in the second information or whether to identify a processing program corresponding to the moving image data identified by the first information. This user interface unit enables the user to readily identify a processing program.

Advantageous Effects of Invention

According to some embodiments of the present technology, a terminal device in a medical institution or the like can obtain high quality still image data by the newest processing program at a low cost, rather than performing image processing by itself. Also, according to the present technology, a terminal device in a medical institution or the like can obtain still images with not only the newest processing program, but with an optional processing program, and can favorably handle chronological observations at a medical institution or the like.

BRIEF DESCRIPTION OF DRAWINGS

FIG. 5 is a diagram illustrating examples of search information transmitted from the display terminal unit to a server device.

FIG. 6 is a diagram describing processing by the image processing unit.

FIG. 7 is a diagram illustrating examples of sharpness-improving processing performed by the image processing unit.

FIG. 8 is a flowchart describing an example of processing procedures for storing (saving) fundus moving image data in the image processing system.

FIG. 9 is a flowchart describing an example of user operating procedures at a display terminal unit wherein search options cannot be set.

FIG. 10 is a flowchart describing an example of user operating procedures at a display terminal unit wherein search options can be set.

FIG. 11 is a flowchart describing an example of processing procedures at a display terminal unit wherein search options cannot be set.

FIG. 12 is a flowchart describing an example of processing procedures at a display terminal unit wherein search options can be set.

FIG. 13 is a flowchart describing an example of processing procedures of search result (fundus still image data) transmission of a server device.

FIG. 14 is a flowchart describing another example of processing procedures of search result (fundus still image data) transmission of a server device.

FIG. 15 is a flowchart describing an example of search/display processing procedures in the image processing system.

FIG. 17 is a flowchart describing an example of updating processing of saved content in a cache unit on a server device.

FIG. 18 is a flowchart describing another example of updating processing of saved content in a cache unit on a server device.

FIG. 19 is a flowchart describing yet another example of updating processing of saved content in a cache unit on a server device.

FIG. 20 is a flowchart describing an example of processing procedures of search result (fundus still image data) transmission of a server device.

FIG. 21 is a flowchart describing another example of processing procedures of search result (fundus still image data) transmission of a server device.

FIG. 22 is a flowchart describing an example of search/display processing procedures in the image processing system.

DESCRIPTION OF EMBODIMENTS

Figure 1:
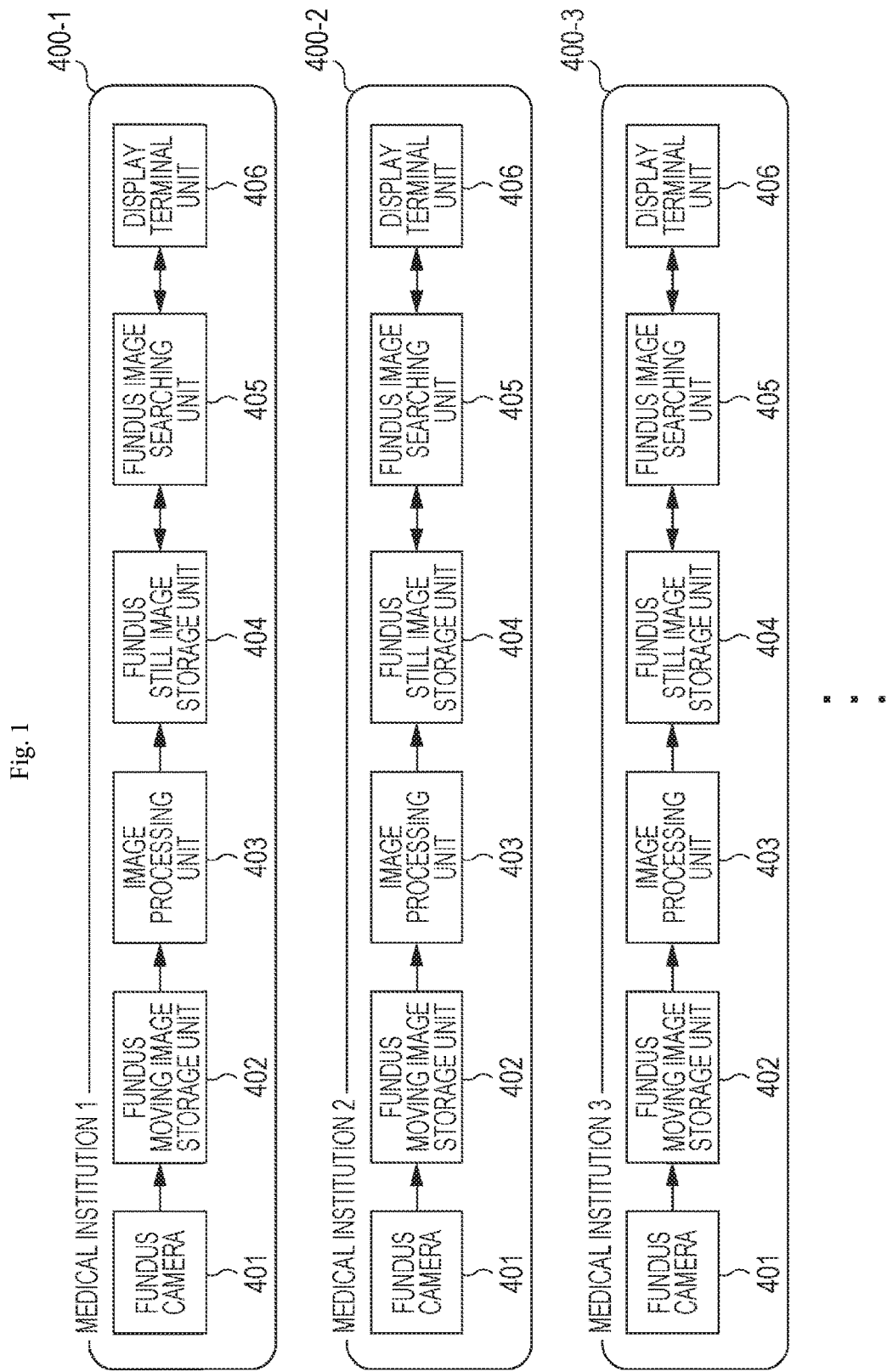
FIG. 1 is a block diagram illustrating a configuration example of an image processing system in medical institutions.

Embodiments of the present disclosure (hereafter, "embodiments") will be described below. Note that description will be given in the following order.
1. First Embodiment
2. Second Embodiment
3. Modification First, an example of an image processing system will be described. FIG. 1 shows a configuration example of an image processing system provided to medical institutions. In FIG. 1, an image processing system 400-1, 400-2, 400-3, and the like are provided to a medical institution 1, medical institution 2, and medical institution 3, respectively.

The image processing system 400 (400-1, 400-2, 400-3, and the like) will be described. The image processing system 400 has a fundus camera 401, fundus moving image storage unit 402, image processing unit 403, fundus still image storage unit 404, fundus image searching unit 405, and display terminal unit 406.

The fundus camera 401 photographs a fundus image as a moving image. The fundus moving image storage unit 402 temporarily stores the moving image data of the fundus image obtained by photographing with the fundus camera 401. The fundus moving image storage unit 402 is made up of storage such as an HDD or the like. The image processing unit 403 generates fundus still image data from the moving image data stored in the fundus moving image storage unit 402. In the image processing unit 403, at least one of NR (noise reduction), sharpness improvement, and DR (dynamic range) improvement will be executed, and high quality fundus still image data is generated.

The fundus still image storage unit 404 stores data of the fundus still image generated by the image processing unit 403. The fundus image searching unit 405 searches, from the fundus still image storage unit 404, for fundus still image data corresponding to the search information (user ID, photograph date and time, etc.) that is transmitted from the display terminal unit 406, reads out the fundus still image data from the fundus still image storage unit 404, and transmits this to the display terminal unit 406. The display terminal unit 406 transmits the search information to the fundus image searching unit 405, receives the fundus still image data transmitted from the fundus image searching unit 405, and displays a desired fundus still image.

Figure 2:
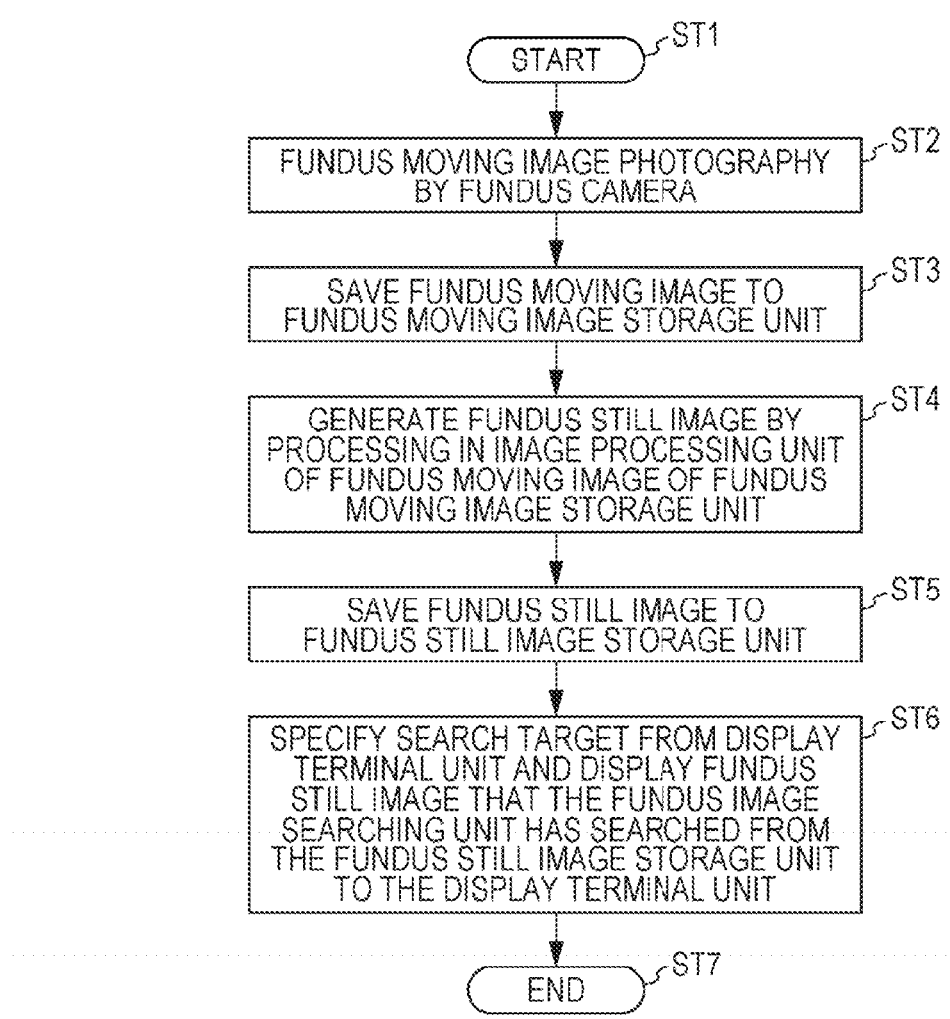
FIG. 2 is a flowchart describing the flow of processing of the image processing system.

The flowchart in FIG. 2 shows the processing flow of the image processing system 400 (400-1, 400-2, 400-3, and the like). In step ST1 the image processing system 400 starts the processing. Next, in step ST2 the image processing system 400 photographs a fundus moving image with the fundus camera 401. In step ST3, the image processing system 400 then saves (stoles) the fundus moving image data obtained by photographing in the fundus moving image storage unit 402.

Next, in step ST4 the image processing system 400 performs processing at the image processing unit 403 as to the fundus moving image data stored in the fundus moving image storage unit 402, thereby generating fundus still image data. In step ST5, the image processing system 400 saves (stores) the fundus still image data generated by the image processing unit 403 in the fundus still image storage unit 404.

Next, in step ST6 the image processing system 400 specifies a search target from the display terminal unit 406, i.e. transmits the search information from the display terminal unit 406 to the fundus image searching unit 405. Also, in step ST6 the image processing system 400 transmits the fundus still image data that the fundus image searching unit 405 has searched for from the fundus still image storage unit 404 to the display terminal unit 406, and displays the fundus still image on the display terminal unit 406. In step ST7 the image processing system 400 ends the processing.

In the image processing systems 400, fundus still image data is generated from the fundus moving image data by image processing, whereby high quality fundus still image data can be obtained. In this case, the image quality of the fundus still image depends on the performance of the image processing algorithm. In the case that a new image processing algorithm is developed, updates to the hardware or software (processing process) has to be made in the image processing systems 400, resulting in high costs for the updates.

<1. First Embodiment>

"Configuration Example of Image Processing System"

Figure 3:
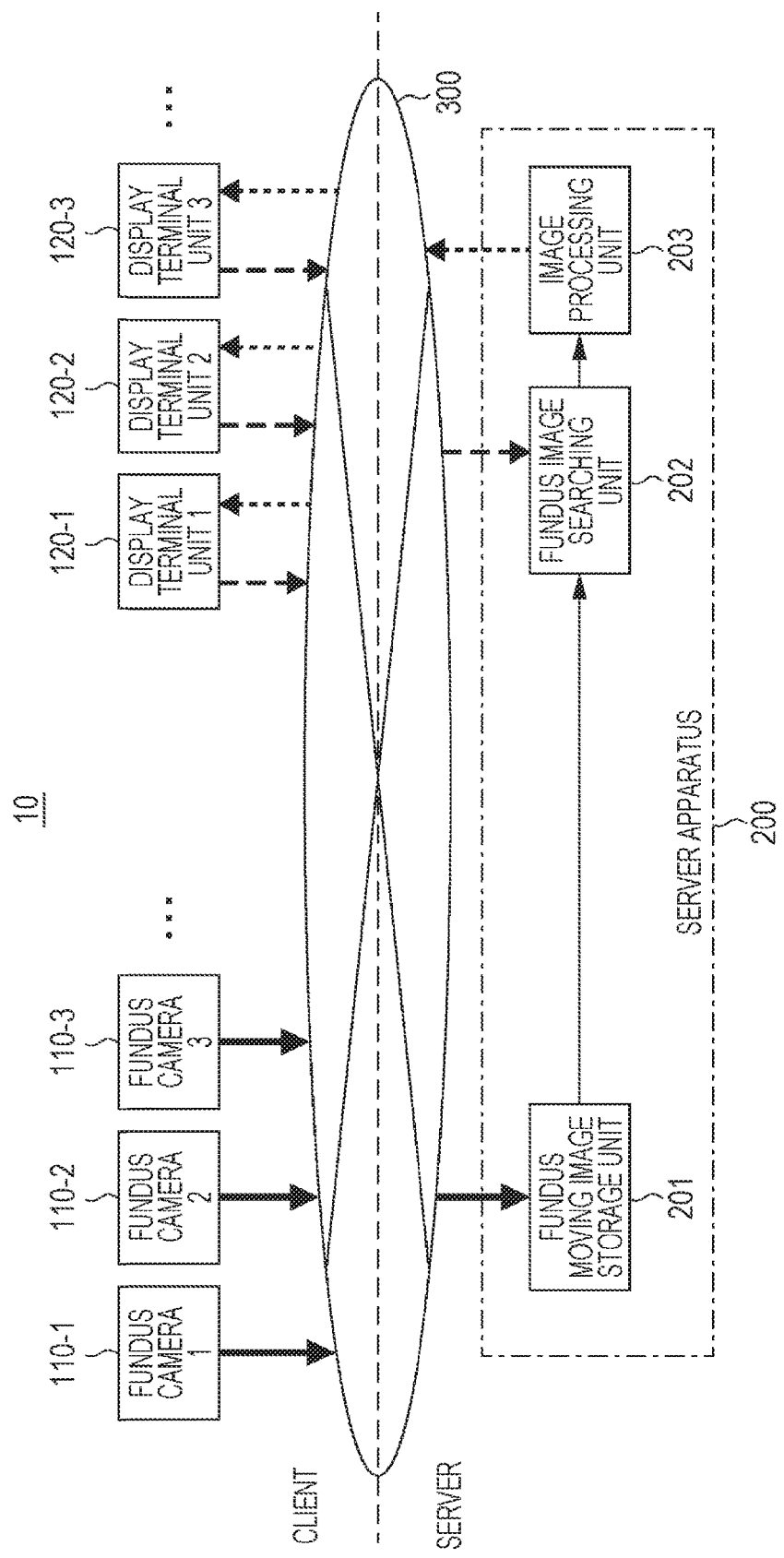
FIG. 3 is a block diagram illustrating a configuration of an image processing system according to a first embodiment.

FIG. 3 shows a configuration example of an image processing system 10 according to a first embodiment of the present technology. This image processing system 10 is made up of a server device 200 and terminal device being connected via a network 300. The fundus cameras 110-1, 110-2, 110-3, and the like and display terminal units 120-1, 120-2, 120-3, and the like each configure a terminal device. The fundus camera and terminal display unit may be considered to exist, not only independently as shown in the diagram, but also so as to be integrated together.

The fundus cameras 110-1, 110-2, 110-3, and the like photograph a fundus image as a moving image and transmit the fundus moving image data obtained by photographing to the server device 200 via the network 300. The display terminal units 120-1, 120-2, 120-3, and the like transmit the search information to the server device 200 via the network 300. Also, the display terminal units 120-1, 120-2, 120-3, and the like receive the fundus still image data corresponding to the search information, which is transmitted from the server device 200 via the network 300, and displays this on a display.

The search information will now be described. First information that identifies the fundus moving image data and second information that identifies the processing program are included in the search information. Now, there may be cases wherein the examiner desires to perform past observations of images seen in the past used for examination in the past. For example, the display terminal units 120-1, 120-2, 120-3, and the like may be provided with a user interface unit to select whether to identify the newest processing program with the second information or whether to identify a processing program corresponding to the fundus moving image data identified with the first information.

Figure 4:
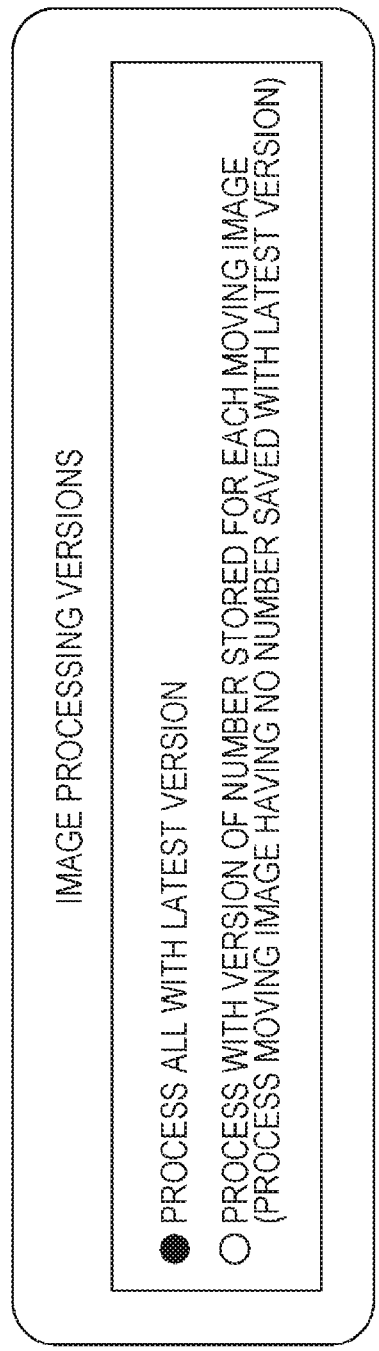
FIG. 4 is a diagram illustrating an example of a GUI for a user interface unit of a display terminal unit to display on a display.

FIG. 4 shows an example of a GUI (Graphical User Interface) wherewith the user interface unit of the display terminal units 120-1, 120-2, 120-3, and the like displays on a display. Upon the user selecting "Process all with newest version" as the image processing version, the second information included in the search information identifies the newest version of the processing program. On the other hand, upon the user selecting "Process with version number saved for each moving image", the second information included in the search information identifies the version of the processing program that corresponds to the fundus moving image data identified with the first information.

FIG. 5 shows an example of search information transmitted from the display terminal units 120-1, 120-2, 120-3, and the like to the server device 200. FIG. 5(*a*) shows an example of personal ID (e.g., information identifying a patient or some other imaged subject and photograph date period (e.g., April 1990 to current, etc.) information that is included in the search information. In this example, the personal ID and photograph date period make up the first information to identify the fundus moving image data. Also, in this example, there is no image processing version number information, which makes up the second information and identifies the newest processing program.

FIG. 5(*b*) shows an example of personal ID, photograph date and time, and image processing version number information that is included in the search information. In this example, the personal ID and photograph date and time makes up the first information to identify the fundus moving image data. Also, in this example, the image processing version number makes up the second information to identify the processing program.

The server device 200 has a fundus moving image storage unit 201, fundus image searching unit 202, and image processing unit 203. The fundus moving image storage unit 201 stores the fundus moving image data transmitted from the fundus cameras 110-1, 110-2, 110-3, and the like, via the network 300. The fundus moving image data stored thus in the fundus moving image storage unit 201 has information such as personal ID, photograph date and time, etc. appended thereto for searching. The fundus image searching unit 202 searches for and reads out the fundus moving image data corresponding to the search information from the fundus moving image storage unit 201, and transmits this to the image processing unit 203.

The image processing unit 203 can automatically update or add a processing program. That is to say, in the case that a new image processing algorithm is developed, updating or adding of the processing program is performed. According to this embodiment, adding of the processing program is performed. That is to say, while the old version of the processing program remains, a new version of the processing program is added.

The image processing unit 203 processes the fundus moving image data transmitted from the fundus image searching unit 202 with the processing program identified by the search information to generate the fundus still image data. The image processing unit 203 then transmits the generated fundus still image data to the display terminal unit 120 which is the transmission source of the search information, via the network 300.

Now, processing by the image processing unit 203 will be further described. As shown in FIG. 6, the image processing unit 203 executes one or more of NR (noise reduction), sharpness improvement, and DR (dynamic range) improvement, and from the data Vin of the fundus moving image, generates high quality data Vout of the fundus still image. As sharpness improvement processing, the image processing unit 203 uses reconfiguration-type super-resolution processing, learning-type super resolution processing, or blurring removal processing, for example, as shown in FIGS. 7 (*a*), (*b*), and (*c*).

The reconfiguration-type super-resolution processing is processing to layer the image data of multiple frames, based on the moving image data, thereby generating high quality still image data wherein the dynamic range has been extended. Also, the learning-type super-resolution processing is processing to perform super-resolution processing using a dictionary that has been generated through learning, and generates high quality still image data. While detailed descriptions will be omitted, the reconfiguration-type super-resolution processing and learning-type super-resolution processing are described in Japanese Patent Application No. 2010-258556 by the present applicant.

The blurring removal processing is processing to cancel blurring in an image and generate a sharp image, using blind deconvolution, for example. The blurring removal processing will be further described.

Let us say that a Point Spread Function (PSF) that expresses the input/output properties of an optical system is represented by $h(x, y)$, the observed image by $g(x, y)$, the true image by $f(x, y)$, and Fourier transforms by $H(u, v)$, $G(u, v)$, and $F(u, v)$, respectively. At this time, the following relational expressions hold between these expressions (noise is omitted for simplicity).

$$g(x,y)=h(x,y)*f(x,y)$$

$$G(u,v)=H(u,v)F(u,v)$$

$$G(u,v)=z[g(x,y)]$$

$$H(u,v)=z[h(x,y)]$$

$$F(u,v)=z[f(x,y)]$$

$z[\ ]$: Fourier Transform

In the case the optical system has a blurring property, blurring occurs in the observed image g(x, y). At this time, canceling the blurring of the observed image and obtaining a sharp image (true image: f(x, y)) indicates that f(x, y) is obtained from g(x, y) (F(u, v) is obtained from G(u, v)). This processing is called deconvolution. If h(x, y) (or H(u, v)) is a known value, deconvolution can be performed, but if not a known value, this value has to be estimated.

A method for obtaining an image without blurring f(x, y) from a blurred image g(x, y) that has been photographed in the case that h(x, y) (or H(u, v)) is not a known value is blind deconvolution. This is a method to simultaneously estimate f(x, y) and h(x, y) based on some sort of a priori information relating to the non-blurring image f(x, y) and point spread function h(x, y).

Blind deconvolution is used for blurring removal processing, for example. The following is an example of a document relating to a specific method of blind deconvolution, for example.

G. R. Ayers and J. C. Dainty: "Iterative blind deconvolution method and its applications," Optics Letters, Vol. 13, pp. 547-549 (1988)

The operations of the image processing system 10 shown in FIG. 3 will be described. First, the storage (saving) processing of fundus moving image data in the image processing system 10 will be described. The flowchart in FIG. 8 shows an example of the processing procedures thereof. In step ST11 the image processing system 10 starts the processing. In step ST12, the fundus camera 110 (110-1, 110-2, 110-3, and the like) photographs the fundus image as a moving image.

Next, in step ST13, the fundus camera 110 transmits the fundus moving image data obtained by photographing to the server device 200 via the network 300. Also, in step ST13, the server device 200 stores (saves) the fundus moving image data transmitted from the fundus camera 110 in the fundus moving image storage unit 201. In step ST14 the image processing system 10 ends the processing.

Next, operations for fundus still image observation by a user of the display terminal unit 120 (120-1, 120-2, 120-3, and the like) will be described. The flowchart in FIG. 9 shows an example of operating procedures by a user of a display terminal unit 120 wherein processing program version selection (hereafter called "search option setting"), such as described with reference to FIG. 4 above, cannot be made.

In step ST21 the user starts the operations for fundus still image observation. In step ST22, the user specifies a search target. In this case, the user specifies the search target by specifying the period of photograph dates, photograph date and time, and so forth, for example. Next, in step ST23, upon a receipt notification of search results (fundus still image data) being displayed on the display, the user displays and observes the fundus still image on the display. In step ST24, the user then ends the operations for fundus still image observation.

The flowchart in FIG. 10 shows an example of user operating procedures of the display terminal 120 wherein search options can be set. In step ST31, the user starts the operation for observing fundus still images. In step ST32 the user determines whether or not to set the search options. When determination has been made to set the search option, in step ST33 the user sets the search option. For example with the GUI shown in FIG. 4 described above, the user selects "Process all with newest version" or "Process with version number saved for each moving image".

Following the operation in step ST33 the user transitions to the operation in step ST34. Note that upon determining not to set the search option in step ST32, the user immediately transitions to the option in step ST34. In step ST34 the user specifies the search target. In this case, the user specifies a search target by specifying a period of photograph dates, the photograph date and time, or the like, for example. Next, in step ST35, upon a receipt notification of the search result (fundus still image data) being displayed on the display, the user displays and observes the fundus still image on the display. In step ST36, the user ends the operation for fundus still image observation.

Next, processing procedures for transmission of the search information of the display terminal unit 120 and reception of the search result (fundus still image data) will be described. The flowchart in FIG. 11 shows an example of processing procedures of a display terminal unit 120 wherein search options cannot be set. In step ST41, the display terminal unit 120 starts the processing. In step ST42 the display terminal unit 120 transmits the search information (search request) to the server device 200 via the network 300. The search information in this case is in a format such as shown in FIG. 5(a) described above, for example.

Note that cases may be considered wherein the search information is in a format such as shown in FIG. 5(b) described above, for example. For example, the display terminal unit 120 saves the version number of the image processing(processing program) corresponding to the dates and times received in the past as search results. For an image from a date and time that has been searched in the past, the display terminal unit 120 specifies a version number for image processing that has been saved, and for an image from a date and time that has not been searched in the past, a version number indicating "the newest version" is specified and search information is transmitted.

Next, in step ST43, upon receiving the search results (fundus still image data) from the server device 200 via the network 300, the display terminal unit 120 notifies the user that the search results have been received. Note that following this notification, the display terminal unit 120 displays the fundus still image on a display, automatically or based on operation by the user. Following the processing in step ST43, the display terminal unit 120, in step ST44 the processing is ended.

The flowchart in FIG. 12 shows an example of processing procedures of a display terminal unit 120 wherein search options can be set. In step ST51 the display terminal unit 120 starts the processing. In step ST52 the display terminal unit 120 determines which of "Process all with newest version" or "Process with version number saved for each moving image" has been set.

When "Process all with newest version" is set, in step ST53 the display terminal unit 120 transmits search information in a format such as that shown in FIG. 5(b), for example, to the server device 200 via the network 300. In this case, the newest version number that can be processed with the server device 200 is written into "image processing version number" in the search information. Note that in this case, only the newest version number is written into "image processing version number", whereby search information in a format such as that shown in FIG. 5(a), for example, may also be transmitted.

On the other hand, when "Process with version number saved for each moving image" has been set, in step ST54 the display terminal unit 120 transmits the search information in a format such as that shown in FIG. 5(b), for example, to the server device 200 via the network 300. In this case, if there is a version number saved as to the photograph date and time, the number thereof is written in the "image processing version number" in the search information, and if none, the newest version number that can be processed with the server device 200 is written therein.

Following the processing in step ST53 or step ST54, the display terminal unit 120 transitions to the processing in step ST55. In step ST55, upon receiving the search result (fundus still image data) from the server device 200 via the network 300, the display terminal unit 120 saves the "image processing version number" of the received fundus still image data.

Next, in step ST56 the display terminal unit 120 notifies the user of the receipt of the search results. Note that following this notification, the display terminal unit 120 displays the fundus still image on a display, automatically or based on user operations. Following the processing in step ST56, in step ST57 the display terminal unit 120 ends the processing.

Note that the processing procedures shown in the flowchart in FIG. 12 are configured so that the display terminal unit 120 saves the image processing version number corresponding to the photograph date and time. However, the server device 200 may save a combination of the photograph date and time and the image processing version numbers, corresponding to each display terminal unit 120.

Next, processing procedures of the search result (fundus still image data)transmission of the server device 200 will be described. The flowchart in FIG. 13 shows an example of processing procedures of the server device 200 in the case that search information is supplied for the display terminal unit 120 in a format such as shown in FIG. 5(a).

In step ST61 the server device 200 starts the processing. In step ST62, the server device 200 processes the fundus moving image data of a photograph date period, of the fundus moving image data stored in the fundus moving image storage unit 201, with the newest version of the processing program in the image processing unit 203, to generate fundus still image data.

Also, in step ST62, the server device 200 transmits the generated fundus still image data as search results to the display terminal unit 120 via the network 300. In this event, the image processing version number is also appended to the still image data. Following the processing in step ST62, in step ST63 the server device 200 ends the processing.

The flowchart in FIG. 14 shows an example or processing procedures of the server device 200 in the case that search information is supplied from the display terminal unit 120 in a format such as shown in FIG. 5(b). In step ST71 the server device 200 starts the processing. In step ST72 the server device 200 processes the fundus moving image data of a photograph date and time, of the moving image data stored in the fundus moving image storage unit 201, with the specified version of the processing program, by the image processing unit 203, to generate fundus still image data.

Also, in step ST72 the server device 200 transmits the generated still image data as search results to the display terminal unit 120 via the network 300. In this event, the image processing version number is also appended to the still image data. Note that in the case that a specified version of a processing program is not installed in the image processing unit 203, and processing thereby cannot be performed, processing is performed with the processing program having the nearest version to the specified version. Following the processing in step ST72, in step ST73 the server device 200 ends the processing.

In the event of transmitting the fundus still image data that has been processed and obtained with a version different from the version specified as described above to the display terminal unit 120 as search results, in order to clarify the fact thereof, a warning message may be appended.

Next, search/display processing in the image processing system 10 will be described. The flowchart in FIG. 15 shows an example of the processing procedures thereof. In step ST81 the image processing system 10 starts the processing. In step ST82 the search target is specified by the display terminal unit 120. That is to say, the search information (see FIGS. 5(a) and (b)) is transmitted to the server device 200 via the network 300.

Next, in step ST83 the fundus image searching unit 202 of the server device 200 searches for the data of the fundus moving image corresponding to the search information from the fundus moving image storage unit 201, and supplies this to the image processing unit 203. In step ST84 the image processing unit 203 of the server device 200 processes the fundus moving image data with a processing program of a version corresponding to the search information, to generate fundus still image data. Also, in step ST84 the server device 200 transfers the fundus still image data generated by the image processing unit 203 as search results to the display terminal unit 120 which is the transmission source of the search information, via the network 300.

Next, in step ST85, the display terminal unit 120 displays the fundus still image on the display, based on the fundus still image data transferred from the server device 200. Following the processing in step ST85, the image processing system 10 ends the processing in step ST86.

As described above, in the image processing system 10 shown in FIG. 3, the image processing unit 203 of the server device 200 can automatically modify or add a processing program. Search information is transmitted from the display terminal unit 120 serving as a terminal device to the server device 200, and fundus moving image data corresponding to the search information is searched for in the fundus moving image storage unit 201 and supplied to the image processing unit 203. In the image processing unit 203, the fundus moving image data is processed by a processing program of a version corresponding to the search information, and fundus still image data is generated and transmitted to the display terminal unit 120.

The display terminal units 120 do not perform image processing by themselves, but can obtain high quality still image data by the newest processing algorithm at a low cost. Also, the display terminal units 120 can obtain still images with not only the newest version of the processing program, but with an optional version of a processing program, and can be favorably applied to past observations such as medical images or the like.

<2. Second Embodiment>

"Configuration Example of Image Processing System "

Figure 16:
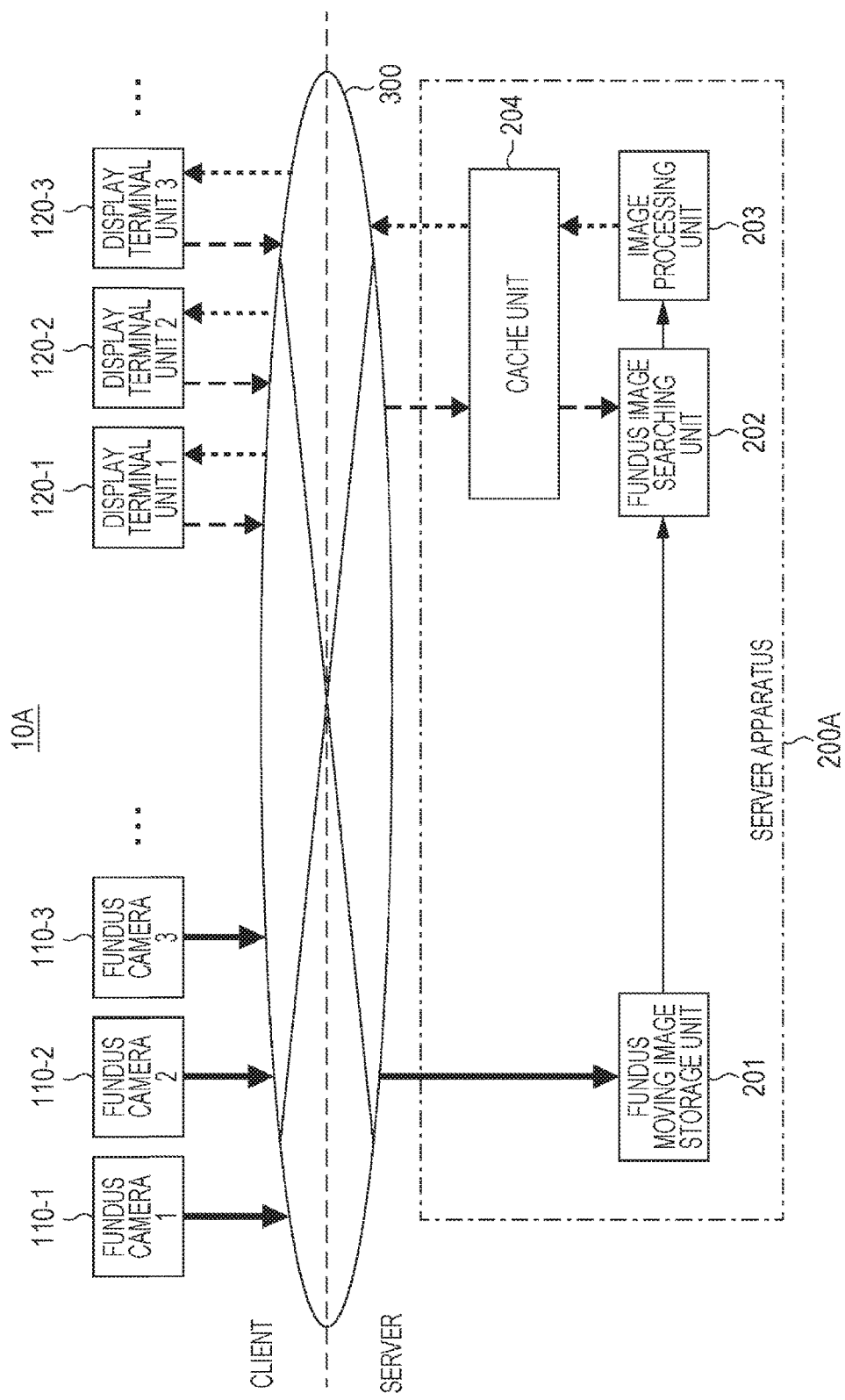
FIG. 16 is a block diagram illustrating a configuration example of an image processing system according to a second embodiment.

FIG. 16 shows a configuration example of an image processing system 10A according to a second embodiment of the present technology. In FIG. 16, the portions corresponding to FIG. 3 have the same reference numerals appended thereto, and detailed descriptions thereof will be omitted as appropriate. The image processing system 10A is made up with a server device 200A and terminal device being connected via the network 300. The fundus cameras 110-1, 110-2, 110-3, and the like and the display terminal units 120-1, 120-2, 120-3, and the like each configure a terminal device. The fundus camera and terminal display unit may be considered to exist, not only independently as shown in the diagram, but also so as to be integrated together.

The fundus cameras 110-1, 110-2, 110-3, and the like photograph a fundus image as a moving image and transmit the fundus moving image data obtained by photographing to the server device 200A via the network 300. The display terminal units 120-1, 120-2, 120-3, and the like transmit the search information (see FIGS. 5(*a*) and (*b*)) to the server device 200A via the network 300. Also, the display terminal units 120-1, 120-2, 120-3, and the like receive the fundus still image data corresponding to the search information, which is transmitted from the server device 200A via the network 300, and displays this on a display.

The server device 200A has a fundus moving storage unit 201, fundus image searching unit 202, image processing unit 203, and cache unit 204. The fundus moving storage unit 201 stores the fundus moving image data that is transmitted from the fundus cameras 110-1, 110-2, 110-3, and the like via the network 300. Information such as a personal ID, photograph date and time and so forth are appended to the fundus moving image data stored in the fundus moving image storage unit 201, for searching.

The image processing unit 203 can automatically update or add a processing program. That is to say, in the case that a new image processing algorithm is developed, updating or adding of the processing program is performed. According to this embodiment, adding of the processing program is performed. That is to say, while the old version of the processing program remains, a new version of the processing program is added.

The image processing unit 203 processes the fundus moving image data transmitted from the fundus image searching unit 202 with the processing program identified by the search information, to generate the fundus still image data. The cache unit 204 holds the fundus still image data generated by the image processing unit 203. When the fundus still image data corresponding to the search information is being held in the cache unit 204, the server device 200A retrieves the fundus still image data from the cache unit 204 and transmits this to the display terminal unit which is the transmission source of the search information via the network 300.

When the fundus still image data corresponding to the search information is not held in the cache unit 204, the fundus image searching unit 202 searches and reads out the fundus moving image data corresponding to the search information from the fundus moving image storage unit 201, and transmits this to the image processing unit 203. On the other hand, when the fundus still image data corresponding to the search information is not held in the cache unit 204, the server device 200A transmits the fundus still image data corresponding to the search information generated by the image processing unit 203 to the display terminal unit which is the transmission source of the search information, via the network 300.

For example, fundus still image data, which is fundus moving image data stored in the fundus moving image storage unit 201 that has been processed and generated by the newest version of the processing program in the image processing unit 203, is held in the cache unit 204. The flowchart in FIG. 17 shows an example of updating processing of the held content in the cache unit 204 in the server device 200A.

In step ST91 the server device 200A starts the processing. In step ST92, the server device 200A determines whether or not a new version of the processing program (new algorithm) has been installed in the image processing unit 203. When a new version of the processing program has been installed, in step ST93 the server device 200A deletes all of the fundus still image data generated by the past processing programs held in the cache unit 204.

In step ST94, the server device 200A processes all of the fundus moving image data existing in the fundus moving image storage unit 201 with the new version of the processing program in the image processing unit 203, generates fundus still image data, and saves this in the cache unit 204. Following the processing in step ST94, the server device 200A returns to the processing in step ST92.

On the other hand, when a new version of the processing program is not installed in the image processing unit 203 in step ST92, in step ST95 the server device 200A determines whether or not fundus moving image data has been added to the fundus moving image storage unit 201. When fundus moving image data has not been added, the server device 200A immediately returns to the processing in step ST92.

When fundus moving image data has been added in step ST95, the server device 200A transitions to the processing in step ST96. In step ST96 the server device 200A processes all of the added fundus moving image data with the newest version of the processing program in the image processing unit 203 to generate fundus still image data, and saves this in the cache unit 204. Following the processing in step ST96, the server device 200A returns to the processing in step ST92.

Also, for example, fundus still image data, which is fundus moving image data stored in the fundus moving image storage unit 201 that has been processed and generated by all of the processing programs in the image processing unit 203, is held in the cache unit 204. The flowchart in FIG. 18 shows an example of updating processing of the held content in the cache unit 204 in the server device 200A.

In step ST101, the server device 200A starts the processing. In step ST102, the server device 200A determines whether or not a new version of the processing program (new algorithm) has been installed in the image processing unit 203. When a new version of the processing program has been installed, the server device 200A transitions to the processing in step ST103.

In step ST103, the server device 200A processes all of the fundus moving image data existing in the fundus moving image storage unit 201 with the new version of the processing program in the image processing unit 203, generates fundus still image data, and saves this in the cache unit 204. Following the processing in step ST103, the server device 200A returns to the processing in step ST102.

On the other hand, when a new version of the processing program is not installed in the image processing unit 203 in step ST102, in step ST104 the server device 200A determines whether or not fundus moving image data has been added to the fundus moving image storage unit 201. When fundus moving image data has not been added, the server device 200A immediately returns to the processing in step ST102.

When fundus moving image data has been added in step ST104, the server device 200A transitions to the processing in step ST105. In step ST105 the server device 200A processes all of the added fundus moving image data with all of the processing programs in the image processing unit 203 to generate fundus still image data, and saves this in the cache unit 204. Following the processing in step ST105, the server device 200A returns to the processing in step ST102.

Further, for example, the fundus still image data that has been generated in the past by the image processing unit 203 and transferred to the cache unit 204, then transmitted to the display terminal unit at the transmission source of the search information via the network 300, is held in the cache unit 204. The flowchart in FIG. 19 shows an example of the updating processing of the holding content in the cache unit 204 in the server device 200A.

In step ST111 the server device 200A starts the processing. In step ST112, the server device 200A determines whether or not there is any fundus still image data that has been transferred from the image processing unit 203 to the cache unit 204. When there is no fundus still image data transferred from the image processing unit 203 to the cache unit 204, the server device 200A immediately returns to the processing in step ST112.

On the other hand, when there is fundus still image data that has been transferred to the cache unit 204 from the image processing unit 203, the server device 200A transitions to the processing in step ST113. In step ST113 the server device 200A saves the transferred fundus still image data to the cache unit 204. Following the processing in step ST113, the server device 200A returns to the processing in step ST112.

Note that in the event of following the procedures of the updating processing shown in the flowchart in FIG. 19, at the point in time that the data amount within the cache unit 203 has exceeded a fixed value determined beforehand, the fundus still image data having the earliest point-in-time of being saved to the cache unit 204 may be deleted.

The operations of the image processing system 10A shown in FIG. 16 will be described. The processing for storing (saving) the fundus moving image data in the image processing system 10A is similar to the storage (saving) processing in the image processing system 10 shown in FIG. 3 (see FIG. 8). Also, the user operations for fundus still image observation of the display terminal unit 120 in the image processing system 10A is similar to the user operations of the image processing system 10 shown in FIG. 3 (see FIG. 9 and FIG. 10). Further, the processing procedures of the search information transmission and search result (fundus still image data) reception of the display terminal unit 120 in the image processing system 10A are similar to the processing procedures in the image processing system 10 shown in FIG. 3 (see FIGS. 11 and 12).

The processing procedures of search result (fundus still image data) transmission of the server device 200A will be described. The flowchart in FIG. 20 shows an example of processing procedures of the server device 200A in the case that search information is supplied from the display terminal unit 120 in a format such as shown in FIG. 5(*a*).

In step ST121 the server device 200A starts the processing. In step ST122, when there is fundus still image data in the cache unit 204 corresponding to the search information, the server device 200A sets the fundus still image data thereof as the search results. Also, in step ST122, when there is no fundus still image data in the cache unit 204 corresponding to the search information, the server device 200A sets the following as the search results. That is to say, of the fundus moving image data stored in the fundus moving image storage unit 201, the fundus still image data generated by processing the fundus image data from a period of photograph dates with the newest version of the processing program in the image processing unit 203, is set as the search results.

In step ST122, the server device 200A transmits the fundus still image data serving as the search results to the display terminal unit 120 which is the transmission source of the search information, via the network 300. In this event, the version number of the image processing is also appended to the still image data. Following the processing in step ST122, in step ST123 the server device 200A ends the processing.

The flowchart in FIG. 21 shows an example of the processing procedures of the server device 200A in the case that search information is supplied from the display terminal unit 120 in a format such as shown in FIG. 5(*b*). In step ST131, the server device 200A starts the processing. In step ST132, when there is fundus still image data in the cache unit 204 corresponding to the search information, the server device 200A sets the fundus still image data thereof as the search results.

Also, in step ST132, when there is no fundus still image data in the cache unit 204 corresponding to the search information, the server device 200A sets the following as the search results. That is to say, of the fundus moving image data stored in the fundus moving image storage unit 201, the server device 200A processes the fundus moving image data of a photograph date and time with the version of the processing program specified by the image processing unit 203, and sets the generated fundus still image data as the search results.

Note that in the case that no processing program of a version specified by the search information has been installed, the server device 200A sets the following as the search results. That is to say, of the fundus still images that can be generated by the image processing unit 203 or the fundus still images in the cache unit 204, the fundus still image data generated by the processing program of the version nearest the specified version is set by the server device 200A as the search results.

Also, in step ST132, the server device 200A transmits the fundus still image data serving as the search results to the display terminal unit 100 which is the transmission source of the search information, via the network 300. In this event, the image processing version number is also appended to the still image data. Following the processing in step ST132, in step ST133 the server device 200A ends the processing.

Next, the search/display processing in the image processing system 10A will be described. The flowchart in FIG. 22 shows an example of the processing procedures thereof. In step ST141 the image processing system 10A starts the processing. In step ST142 the search target is specified from the display terminal unit 120. That is to say, the display terminal unit 120 transmits the search information (see FIGS. 5(*a*) and (*b*)) to the server device 200A via the network 300.

Next, in step ST143 the server device 200A determines whether or not there is any fundus still image data in the cache unit 204 corresponding to the search information. When there is fundus still image data in the cache unit 204 corresponding to the search information, the server device 200A sets the fundus still image data thereof as the search results, and transitions to the processing in step ST147.

When there is no fundus still image data in the cache unit 204 corresponding to the search information, the server device 200A transitions to the processing in step ST144. In step ST144, the cache unit 204 of the server device 200A transfers the search information to the fundus image searching unit 202. In step ST145, the fundus image searching unit 202 of the server device 200A searches for the fundus moving image data corresponding to the search information from the fundus moving image storage unit 201, and supplies this to the image processing unit 203.

In step ST146, the image processing unit 203 of the server device 200A processes the fundus moving image data with the processing program of a version corresponding to the search information to generate fundus still image data, and transfers this, as the search results, to the cache unit 204. Following the processing in step ST146, the server device 200A transitions to the processing in step ST147.

In step ST147, the cache unit 204 of the server device 200A transfers the fundus still image data serving as the search results to the display terminal unit 120 which is the transmission source of the search information, via the network 300. In step ST148, the display terminal unit 120 displays the fundus still image on a display, based on the fundus still image data transferred from the server device 200A. Following the processing in step ST148, in step ST149 the image processing system 10A ends the processing.

As described above, in the image processing system 10A shown in FIG. 16, the image processing unit 203 of the server device 200A can automatically modify or add a processing program. Search information is transmitted from the display terminal unit 120 serving as a terminal device to the server device 200A, and fundus still image data corresponding to the search information is transmitted from the server device 200A to the display terminal unit 120. The display terminal units 120 do not perform image processing by themselves, but can obtain high quality still image data by the newest processing algorithm at a low cost. Also, the display terminal units 120 can obtain still images with not only the newest version of the processing program, but with an optional version of a processing program, and can be favorably applied to past observations such as medical images or the like.

Also, in the image processing system 10A shown in FIG. 16, a cache unit 204 to hold the fundus still image data is provided to the server device 200A. In the case there is fundus still image data in the cache unit 204 corresponding to the search information, the fundus still image data is retrieved and transmitted to the display terminal unit 120. Accordingly, the fundus still image data existing already in the cache unit 204 does not have to be generated with the image processing unit 203, and the still image data corresponding to the search information can be efficiently transmitted to the display terminal unit 120.

<3. Modification>

Note that according to the above-described embodiments, examples have been giving of handling a fundus image as an image. However, it goes without saying that the present technology can similarly be applied to other medical images, and further, images other than medical images, such as monitoring images, for example. The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware, or with general purpose hardware (e.g., one or more processors) that is programmed using microcode or software to perform the functions recited above. In this respect, it should be appreciated that one implementation of embodiments of the present invention comprises at least one computer-readable storage medium (i.e., a tangible, non-transitory computer-readable medium, such as a computer memory, a floppy disk, a compact disk, a magnetic tape, or other tangible, non-transitory computer-readable medium) encoded with a computer program (i.e., a plurality of instructions), which, when executed on one or more processors, performs above-discussed functions of embodiments of the present invention. The computer-readable storage medium can be transportable such that the program stored thereon can be loaded onto any computer resource to implement aspects of the present invention discussed herein. In addition, it should be appreciated that the reference to a computer program which, when executed, performs any of the above-discussed functions, is not limited to an application program running on a host computer. Rather, the term "computer program" is used herein in a generic sense to reference any type of computer code (e.g., software or microcode) that can be employed to program one or more processors to implement above-discussed aspects of the present invention.

Also, various embodiments of the present technology can assume configurations such as described below.

1. An apparatus comprising at least one processor programmed to:

transmit, via at least one network, a request to another apparatus for still image data generated from moving image data, the request comprising at least one criterion; and receive still image data generated from moving image data matching the at least one criterion in the request.

2. The apparatus of configuration 1, wherein the at least one processor is further programmed to:

include in the request information identifying at least one image processing technique for use in generating the moving image data from the still image data.

3. The apparatus of configuration 2, wherein the information identifying the at least one image processing technique comprises an identifier for a version of an image processing program for use in generating the still image data from the moving image data.

4. The apparatus of configuration 3, further comprising at least one input device, wherein the at least one processor is further programmed to:

receive user input via the at least one input device; and select the version of the image processing program based at least in part on the user input.

5. The apparatus of configuration 2, wherein the information identifying the at least one image processing technique comprises an indication that a newest image processing technique is to be used in generating the still image data from the moving image data.

6. The apparatus of configuration 5, wherein the information identifying the at least one image processing technique comprises an indication that a newest version of an image processing program be used in generating the still image data from the moving image data.

7. The apparatus of configuration 2, wherein the at least one image processing technique comprises an image processing technique selected from a group consisting of: reconfiguration-type super-resolution processing, learning-type super-resolution processing, and blurring removal processing.

8. The apparatus of configuration 1, further comprising at least one imaging device configured to capture a moving image and thereby generate the moving image data, wherein the at least one processor is further programmed to:
transmit the moving image data to the other apparatus.

9. The apparatus of configuration 8, wherein the at least one imaging device comprises at least one medical imaging device configured to capture a moving image from an observation target.

10. The apparatus of configuration 9, wherein the at least one medical imaging device comprises a funduscope configured to capture a moving image from the fundus of an eye of a patient.

11. The apparatus of configuration 1, wherein the at least one processor is further programmed to:
upon receiving the still image data, notify a user that the still image data is available.

12. The apparatus of configuration 1, further comprising at least one display device, wherein the at least one processor is further programmed to:
cause the at least one display device to display a still image to the user based on the still image data.

13. The apparatus of configuration 1, further comprising at least one input device, wherein the at least one processor is further programmed to:
receive user input via the at least one input device; and
determine the at least one criterion based at least in part on the user input.

14. The apparatus of configuration 13, wherein the at least one processor is further programmed to:
receive time information from the user via the at least one input device; and
determine the at least one criterion based at least in part on the time information.

15. The apparatus of configuration 13, wherein the at least one processor is further programmed to:
receive personal identification information from the user via the at least one input device; and
determine the at least one criterion based at least in part on the personal identification information.

16. The apparatus of configuration 15, wherein the moving image data comprises medical moving image data, and wherein the personal identification information comprises information identifying a patient who is a subject of the medical moving image data.

17. An apparatus comprising:
means for transmitting, via at least one network, a request to another apparatus for still image data generated from moving image data, the request comprising at least one criterion; and
means for receiving still image data generated from moving image data matching the at least one criterion in the request.

18. The apparatus of configuration 17, further comprising means for including in the request information identifying at least one image processing technique for use in generating the moving image data from the still image data.

19. The apparatus of configuration 18, wherein the information identifying the at least one image processing technique comprises an identifier for a version of an image processing program for use in generating the still image data from the moving image data.

20. The apparatus of configuration 19, further comprising:
means for receiving user input; and
means for selecting the version of the image processing program based at least in part on the user input.

21. The apparatus of configuration 18, wherein the information identifying the at least one image processing technique comprises an indication that a newest image processing technique is to be used in generating the still image data from the moving image data.

22. The apparatus of configuration 21, wherein the information identifying the at least one image processing technique comprises an indication that a newest version of an image processing program is to be used in generating the still image data from the moving image data.

23. The apparatus of configuration 18, wherein the at least one image processing technique comprises an image processing technique selected from a group consisting of: reconfiguration-type super-resolution processing, learning-type super-resolution processing, and blurring removal processing.

24. The apparatus of configuration 17, further comprising:
means for capturing a moving image and thereby generating the moving image data; and
means for transmitting the moving image data to the other apparatus.

25. The apparatus of configuration 24, wherein the means for capturing the moving image comprises means for capturing a medical moving image from an observation target.

26. The apparatus of configuration 25, wherein the means for capturing a medical moving image comprises means for capturing a moving image from the fundus of an eye of a patient.

27. The apparatus of configuration 17, further comprising means for, upon receiving the still image data, notifying a user that the still image data is available.

28. The apparatus of configuration 17, further comprising means for displaying a still image to the user based on the still image data.

29. The apparatus of configuration 17, further comprising:
means for receiving user input; and
means for determining the at least one criterion based at least in part on the user input.

30. The apparatus of configuration 29, wherein the means for receiving user input is configured to receive time information from the user, and wherein the means for determining the at least one criterion is configured to determine the at least one criterion based at least in part on the time information.

31. The apparatus of configuration 29, wherein the means for receiving user input is configured to receive personal identification information from the user, and wherein the means for determining the at least one criterion is configured to determine the at least one criterion based at least in part on the personal identification information.

32. The apparatus of configuration 31, wherein the moving image data comprises medical moving image data, and wherein the personal identification information comprises information identifying a patient who is a subject of the medical moving image data.

33. A method comprising acts of:
transmitting, from a first apparatus to a second apparatus, via at least one network, a request for still image data generated from moving image data, the request comprising at least one criterion; and
receiving still image data generated from moving image data matching the at least one criterion in the request.

34. The method of configuration 33, further comprising:
including in the request information identifying at least one image processing technique for use in generating the moving image data from the still image data.

35. The method of configuration 34, wherein the information identifying the at least one image processing technique comprises an identifier for a version of an image processing program for use in generating the still image data from the moving image data.

36. The method of configuration 35, further comprising:
receiving user input via at least one input device; and
selecting the version of the image processing program based at least in part on the user input.

37. The method of configuration 34, wherein the information identifying the at least one image processing technique comprises an indication that a newest image processing technique is to be used in generating the still image data from the moving image data.

38. The method of configuration 37, wherein the information identifying the at least one image processing technique comprises an indication that a newest version of an image processing program is to be used in generating the still image data from the moving image data.

39. The method of configuration 34, wherein the at least one image processing technique comprises an image processing technique selected from a group consisting of: reconfiguration-type super-resolution processing, learning-type super-resolution processing, and blurring removal processing.

40. The method of configuration 33, further comprising:
capturing a moving image and thereby generating the moving image data;
transmitting the moving image data to the second apparatus.

41. The method of configuration 40, wherein capturing the moving image comprises capturing a medical moving image from an observation target.

42. The method of configuration 41, wherein capturing the medical moving image comprises using a funduscope to capture a moving image from the fundus of an eye of a patient.

43. The method of configuration 33, further comprising:
upon receiving the still image data, notifying a user that the still image data is available.

44. The method of configuration 33, further comprising:
displaying a still image to the user based on the still image data.

45. The method of configuration 33, further comprising:
receiving user input via at least one input device; and
determining the at least one criterion based at least in part on the user input.

46. The method of configuration 45, wherein the user input comprises time information, and wherein determining the at least one criterion comprises determining the at least one criterion based at least in part on the time information.

47. The method of configuration 45, wherein the user input comprises personal identification information, and wherein determining the at least one criterion comprises determining the at least one criterion based at least in part on the personal identification information.

48. The method of configuration 47, wherein the moving image data comprises medical moving image data, and wherein the personal identification information comprises information identifying a patient who is a subject of the medical moving image data.

49. At least one computer-readable storage medium encoded with instructions that, when executed by at least one processor, perform a method comprising acts of:

transmitting, from a first apparatus to a second apparatus, via at least one network, a request for still image data generated from moving image data, the request comprising at least one criterion; and
receiving still image data generated from moving image data matching the at least one criterion in the request.

50. The at least one computer-readable storage medium of configuration 49, wherein the method further comprises:
including in the request information identifying at least one image processing technique for use in generating the moving image data from the still image data.

51. The at least one computer-readable storage medium of configuration 50, wherein the information identifying the at least one image processing technique comprises an identifier for a version of an image processing program for use in generating the still image data from the moving image data.

52. The at least one computer-readable storage medium of configuration 51, wherein the method further comprises:
receiving user input via at least one input device; and
selecting the version of the image processing program based at least in part on the user input.

53. The at least one computer-readable storage medium of configuration 50, wherein the information identifying the at least one image processing technique comprises an indication that a newest image processing technique is to be used in generating the still image data from the moving image data.

54. The at least one computer-readable storage medium of configuration 53, wherein the information identifying the at least one image processing technique comprises an indication that a newest version of an image processing program is to be used in generating the still image data from the moving image data.

55. The at least one computer-readable storage medium of configuration 50, wherein the at least one image processing technique comprises an image processing technique selected from a group consisting of: reconfiguration-type super-resolution processing, learning-type super-resolution processing, and blurring removal processing.

56. The at least one computer-readable storage medium of configuration 55, wherein the method further comprises:
capturing a moving image and thereby generating the moving image data;
transmitting the moving image data to the second apparatus.

57. The at least one computer-readable storage medium of configuration 56, wherein capturing the moving image comprises capturing a medical moving image from an observation target.

58. The at least one computer-readable storage medium of configuration 57, wherein capturing the medical moving image comprises using a funduscope to capture a moving image from the fundus of an eye of a patient.

59. The at least one computer-readable storage medium of configuration 49, wherein the method further comprises:
upon receiving the still image data, notifying a user that the still image data is available.

60. The at least one computer-readable storage medium of configuration 49, wherein the method further comprises:
displaying a still image to the user based on the still image data.

61. The at least one computer-readable storage medium of configuration 49, wherein the method further comprises:
receiving user input via at least one input device; and
determining the at least one criterion based at least in part on the user input.

62. The at least one computer-readable storage medium of configuration 61, wherein the user input comprises time information, and wherein determining the at least one criterion comprises determining the at least one criterion based at least in part on the time information.

63. The at least one computer-readable storage medium of configuration 61, wherein the user input comprises personal identification information, and wherein determining the at least one criterion comprises determining the at least one criterion based at least in part on the personal identification information.

64. The at least one computer-readable storage medium of configuration 63, wherein the moving image data comprises medical moving image data, and wherein the personal identification information comprises information identifying a patient who is a subject of the medical moving image data.

65. An apparatus comprising at least one processor programmed to:

receive, via at least one network, a request from another apparatus for still image data generated from moving image data, the request comprising at least one criterion;

use the at least one criterion in the request to obtain still image data generated from moving image data; and respond to the request by transmitting the obtained still image data.

66. The apparatus of configuration 65, further comprising at least one storage device, wherein the at least one processor is further programmed to:

receive the moving image data from the other apparatus; and store the moving image data in the at least one storage device.

67. The apparatus of configuration 66, wherein the at least one processor is further programmed to:

use a newest version of an image processing program to generate the still image data from the moving image data.

68. The apparatus of configuration 65, further comprising at least one storage device, wherein the at least one processor is further programmed to:

use the at least one criterion to retrieve the moving image data from the at least one storage device; and generate the still image data based at least in part on the moving image data.

69. The apparatus of configuration 65, further comprising at least one storage device, wherein the at least one processor is further programmed to:

use the at least one criterion to retrieve the still image data from the at least one storage device, the still image data having been previously generated based at least in part on the moving image data.

70. The apparatus of configuration 69, wherein the still image data is previously generated still image data, and wherein the at least one processor is further programmed to:

determine whether a new image processing technique is available;

if it is determined that a new image processing technique is available, use the new image processing technique to generate new still image data based at least in part on the moving image data; and replace the previously generated still image data with the new still image data.

71. The apparatus of configuration 65, wherein the request received from the other device comprises information identifying at least one image processing technique, and wherein the at least one processor is further programmed to:

use the identified at least one image processing technique to generate the still image data based at least in part on the moving image data.

72. The apparatus of configuration 71, wherein the information identifying the at least one image processing technique comprises an identifier for a version of an image processing program, and wherein the at least one processor is further programmed to:

determine whether the identified version of the image processing program is available; and if it is determined that the identified version of the image processing program is not available, use a nearest available version of the image processing program to generate the still image data from the moving image data.

73. The apparatus of configuration 71, wherein the at least one image processing technique comprises an image processing technique selected from a group consisting of: reconfiguration-type super-resolution processing, learning-type super-resolution processing, and blurring removal processing.

74. An apparatus comprising:

means for receiving, via at least one network, a request from another apparatus for still image data generated from moving image data, the request comprising at least one criterion;

means for using the at least one criterion in the request to obtain still image data generated from moving image data; and means for responding to the request by transmitting the obtained still image data.

75. The apparatus of configuration 74, further comprising storage means, wherein the means for receiving a request is further configured to:

receive the moving image data from the other apparatus; and store the moving image data in the storage means.

76. The apparatus of configuration 75, further comprising:

means for using a newest version of an image processing program to generate the still image data from the moving image data.

77. The apparatus of configuration 74, further comprising storage means, wherein the means for using the at least one criterion is further configured to:

use the at least one criterion to retrieve the moving image data from the storage means; and generate the still image data based at least in part on the moving image data.

78. The apparatus of configuration 74, further comprising storage means, wherein the means for using the at least one criterion is further configured to:

use the at least one criterion to retrieve the still image data from the storage means, the still image data having been previously generated based at least in part on the moving image data.

79. The apparatus of configuration 78, wherein the still image data is previously generated still image data, and wherein the apparatus further comprises means for:

determining whether a new image processing technique is available:

if it is determined that a new image processing technique is available, using the new image processing technique to generate new still image data based at least in part on the moving image data; and replacing the previously generated still image data with the new still image data.

80. The apparatus of configuration 74, wherein the request received from the other device comprises information identifying at least one image processing technique, and
wherein the means for using the at least one criterion is further configured to:
use the identified at least one image processing technique to generate the still image data based at least in part on the moving image data.

81. The apparatus of configuration 80, wherein the information identifying the at least one image processing technique comprises an identifier for a version of an image processing program, and wherein the means for using the at least one criterion is further configured to:
determine whether the identified version of the image processing program is available; and
if it is determined that the identified version of the image processing program is not available, use a nearest available version of the image processing program to generate the still image data from the moving image data.

82. The apparatus of configuration 80, wherein the at least one image processing technique comprises an image processing technique selected from a group consisting of: reconfiguration-type super-resolution processing, learning-type super-resolution processing, and blurring removal processing.

83. A method comprising acts of:
receiving, via at least one network, a request for still image data generated from moving image data, the request comprising at least one criterion;
using the at least one criterion in the request to obtain still image data generated from moving image data; and
responding to the request by transmitting the obtained still image data.

84. The method of configuration 83, further comprising:
receiving the moving image data via the at least one network; and
storing the moving image data in at least one storage device.

85. The method of configuration 84, further comprising:
using a newest version of an image processing program to generate the still image data from the moving image data.

86. The method of configuration 83, further comprising:
using the at least one criterion to retrieve the moving image data from at least one storage device; and
generating the still image data based at least in part on the moving image data.

87. The method of configuration 83, further comprising:
using the at least one criterion to retrieve the still image data from at least one storage device, the still image data having been previously generated based at least in part on the moving image data.

88. The method of configuration 87, wherein the still image data is previously generated still image data, and wherein the method further comprises:
determining whether a new image processing technique is available;
if it is determined that a new image processing technique is available, using the new image processing technique to generate new still image data based at least in part on the moving image data; and
replacing the previously generated still image data with the new still image data.

89. The method of configuration 83, wherein the request received from the other device comprises information identifying at least one image processing technique, and
wherein the method further comprises:
using the identified at least one image processing technique to generate the still image data based at least in part on the moving image data.

90. The method of configuration 89, wherein the information identifying the at least one image processing technique comprises an identifier for a version of an image processing program, and wherein the method further comprises:
determining whether the identified version of the image processing program is available; and
if it is determined that the identified version of the image processing program is not available, using a nearest available version of the image processing program to generate the still image data from the moving image data.

91. The method of configuration 89, wherein the at least one image processing technique comprises an image processing technique selected from a group consisting of: reconfiguration-type super-resolution processing, learning-type super-resolution processing, and blurring removal processing.

92. At least one computer-readable storage medium encoded with instructions that, when executed by at least one processor, perform a method comprising acts of:
receiving, via at least one network, a request for still image data generated from moving image data, the request comprising at least one criterion:
using the at least one criterion in the request to obtain still image data generated from moving image data; and
responding to the request by transmitting the obtained still image data.

93. The at least one computer-readable storage medium of configuration 92, wherein the method further comprises:
receiving the moving image data via the at least one network; and
storing the moving image data in at least one storage device.

94. The at least one computer-readable storage medium of configuration 93, wherein the method further comprises:
using a newest version of an image processing program to generate the still image data from the moving image data.

95. The at least one computer-readable storage medium of configuration 92, wherein the method further comprises:
using the at least one criterion to retrieve the moving image data from at least one storage device; and
generating the still image data based at least in part on the moving image data.

96. The at least one computer-readable storage medium of configuration 92, wherein the method further comprises:
using the at least one criterion to retrieve the still image data from at least one storage device, the still image data having been previously generated based at least in part on the moving image data.

97. The at least one computer-readable storage medium of configuration 96, wherein the still image data is previously generated still image data, and wherein the method further comprises:
determining whether a new image processing technique is available;
if it is determined that a new image processing technique is available, using the new image processing technique to generate new still image data based at least in part on the moving image data; and
replacing the previously generated still image data with the new still image data.

98. The at least one computer-readable storage medium of configuration 92, wherein the request received from the other device comprises information identifying at least one image processing technique, and wherein the method further comprises:

using the identified at least one image processing technique to generate the still image data based at least in part on the moving image data.

99. The at least one computer-readable storage medium of configuration 98, wherein the information identifying the at least one image processing technique comprises an identifier for a version of an image processing program, and wherein the method further comprises:

determining whether the identified version of the image processing program is available; and if it is determined that the identified version of the image processing program is not available, using a nearest available version of the image processing program to generate the still image data from the moving image data.

100. The at least one computer-readable storage medium of configuration 98, wherein the at least one image processing technique comprises an image processing technique selected from a group consisting of: reconfiguration-type super-resolution processing, learning-type super-resolution processing, and blurring removal processing.

101. A system comprising:

a first apparatus comprising at least one first processor programmed to:

transmit, via at least one network, a request to a second apparatus for still image data generated from moving image data, the request comprising at least one criterion; and the second apparatus, wherein the second apparatus comprises at least one second processor programmed to:

receive, via the at least one network, the request for still image data;

use the at least one criterion in the request to obtain still image data generated from moving image data; and respond to the request by transmitting the obtained still image data to the first apparatus, wherein the at least one first processor is further programmed to:

receive the obtained still image data from the second apparatus.

Various embodiments of the present technology can assume additional configurations such as described below.

<Additional Configuration 1>

A server device comprising:

an image processing unit to generate still image data from moving image data stored in a storage unit, wherein a processing program can be automatically updated or added thereto;

a search information receiving unit to receive search information transmitted from a terminal device;

an image transmission unit to transmit, to said terminal device, still image data generated by processing predetermined moving image data using a predetermined processing program, such still image data corresponding to search information received by said search information receiving unit.

<Additional Configuration 2>

The server device according to Additional configuration 1, further comprising:

a cache unit to hold the still image data generated by said image processing unit; wherein in the case that still image data corresponding to the search information from said terminal device is held in said cache unit, said image transmitting unit removes the still image data from the cache unit and transmits to said terminal device.

<Additional Configuration 3>

The server device according to Additional configuration 2, wherein the still image data, which is generated by processing the moving image data stored in said storage unit with the newest version of the processing program in said image processing unit, is held in said cache unit.

<Additional Configuration 4>

The server device according to Additional configuration 2, wherein the still image data, which is generated by processing the moving image data stored in said storage unit with all of the processing programs in said image processing unit, is held in said cache unit.

<Additional Configuration 5>

The server device according to Additional configuration 2, wherein the still image data transmitted in the past by said image transmitting unit to the terminal device corresponding to the search information from said terminal device is held in said cache unit.

<Additional Configuration 6>

The server device according to Additional configuration 1, wherein first information that identifies said moving image data and second information that identifies said processing program are included in the search information received by said search information receiving unit;

and wherein said image transmitting unit transmits, to said terminal device, the still image data generated by processing the moving image data identified by said first information with a processing program identified by said second information.

<Additional Configuration 7>

The server device according to Additional configuration 1, wherein said storage unit stores moving image data that is transmitted from a terminal device which is the same as or different from said terminal device.

<Additional Configuration 8>

The server device according to Additional configuration 1, wherein said image data is image data of a medical image.

<Additional Configuration 9>

An image transmitting method, comprising:

a step of receiving of search information transmitted from a terminal device; and a step of transmitting, to said terminal device, of still image data, which is generated by processing predetermined moving image data with a predetermined processing program, corresponding to said search information.

<Additional Configuration 10>

A program causing a computer to function as:

search information receiving means to receive search information transmitted from a terminal device; and image transmitting means to transmit, to said terminal device, still image data, which is generated by processing predetermined moving image data with a predetermined processing program, corresponding to the search information received by said search information receiving means.

<Additional Configuration 11>

An image processing system, comprising:

a server device and terminal device connected via a network;

said server device further including an image processing unit to generate still image data from moving image data stored in a storage unit, wherein a processing program can be automatically updated or added thereto;

a search information receiving unit to receive search information transmitted from said terminal device; and an image transmission unit to transmit, to said terminal device, still image data generated by processing predetermined moving image data using a predetermined processing program, such still image data corresponding to search information received by said search information receiving unit; and said terminal device further including a search information transmitting unit to transmit said search information to said server device; and an image receiving unit to receive said still image data corresponding to said search information, which is transmitted from said server device.

<Additional Configuration 12>

A terminal device, comprising:

a search information transmitting unit to transmit, to a server device, search information including first information that identifies moving image data and second information that identifies a processing program to generate still image data from the moving image data; and an image receiving unit to receive the still image data generated by processing predetermined moving image data with a predetermined processing program, corresponding to said search information, said still image data having been transmitted from said server device.

<Additional Configuration 13>

The terminal device according to Additional configuration 12, further comprising:

a user interface unit to select, with said second information, whether to identify the newest processing program or whether to identify a processing program corresponding to the moving image data identified with said first information.

<Additional Configuration 14>

An image receiving method, comprising:

a step of transmitting, to a server device, search information including first information that identifies moving image data and second information that identifies a processing program to generate still image data from the moving image data; and a step of receiving the still image data generated by processing predetermined moving image data with a predetermined processing program, corresponding to said search information, said still image data having been transmitted from said server device.

<Additional Configuration 15>

A program causing a computer to function as:

search information transmitting means to transmit, to a server device, search information including first information that identifies moving image data and second information that identifies a processing program to generate still image data from the moving image data; and image receiving means to receive the still image data generated by processing predetermined moving image data with a predetermined processing program, corresponding to said search information, said still image data having been transmitted from said server device.

The phraseology and terminology used herein is for the purpose of description and should not be regarded as limiting. The use of "including," "comprising," "having," "containing," "involving." and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements from each other. Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

REFERENCE SIGNS LIST

10,10A image processing system
110-1,110-2, 110-3 fundus camera
120-1,120-2, 120-3 display terminal unit
200,200A server device
201 fundus moving image storage unit
202 fundus image searching unit
203 image processing unit
204 cache unit
300 network

The invention claimed is:

1. A method implemented by a first apparatus comprising at least one processor, the method comprising acts of:

receiving first user input specifying at least one image processing technique for use in generating still medical image data from moving medical image data;

receiving second user input specifying at least one criterion for still medical image data generated from moving medical image data;

transmitting, to a second apparatus via at least one network, information identifying the at least one image processing technique specified by the first user input; and transmitting, to the second apparatus via the at least one network, a request to output still medical image data generated from moving medical image data, the still medical image data matching the at least one criterion specified by the second user input, the still medical image data being generated by applying the at least one image processing technique specified by the first user input.

2. The method of claim 1, wherein the at least one criterion includes at least one piece of information selected from a group consisting of: information identifying a patient, a user identifier, a date of imaging, and a time of imaging.

3. The method of claim 1, wherein the moving medical image data comprises moving image data of a patient.

4. The method of claim 3, wherein the moving medical image comprises fundus moving image data of the patient.

5. The method of claim 1, wherein the at least one image processing technique comprises a technique selected from a group consisting of: a noise reduction technique, a sharpness improvement technique, and a dynamic range improvement technique.

6. The method of claim 1, wherein the at least one image processing technique comprises layering a plurality of image frames from the moving medical image data.

7. The method of claim 1, wherein the information identifying the at least one image processing technique comprises information identifying a version of an image processing algorithm performed to generate the still medical image data matching the at least one criterion.

8. The method of claim 1, wherein the first apparatus is a terminal device in a medical institution.

9. The method of claim 8, wherein the second apparatus comprises a server including storage storing the moving medical image data, and wherein the server is located remotely from the terminal device.

10. A first apparatus comprising:
at least one computer-readable storage medium storing executable instructions; and
at least one processor programmed by the executable instructions to:
receive first user input specifying at least one image processing technique for use in generating still medical image data from moving medical image data;
receive second user input specifying at least one criterion for still medical image data generated from moving medical image data;
transmit, to a second apparatus via at least one network, information identifying the at least one image processing technique specified by the first user input; and
transmit, to the second apparatus via the at least one network, a request to output still medical image data generated from moving medical image data, the still medical image data matching the at least one criterion specified by the second user input, the still medical image data being generated by applying the at least one image processing technique specified by the first user input.

11. The first apparatus of claim 10, wherein the at least one criterion includes at least one piece of information selected from a group consisting of: information identifying a patient, a user identifier, a date of imaging, and a time of imaging.

12. The first apparatus of claim 10, wherein the at least one image processing technique comprises a technique selected from a group consisting of: a noise reduction technique, a sharpness improvement technique, and a dynamic range improvement technique.

13. The first apparatus of claim 10, wherein the at least one image processing technique comprises layering a plurality of image frames from the moving medical image data.

14. The first apparatus of claim 10, wherein the information identifying the at least one image processing technique comprises information identifying a version of an image processing algorithm performed to generate the still medical image data matching the at least one criterion.

15. A system comprising a terminal device and a server, wherein the terminal device comprises:
at least one computer-readable storage medium storing executable instructions; and
at least one processor programmed by the executable instructions to:
receive first user input specifying at least one image processing technique for use in generating still medical image data from moving medical image data;
receive second user input specifying at least one criterion for still medical image data generated from moving medical image data;
transmit, to the server via at least one network, information identifying the at least one image processing technique specified by the first user input; and
transmit, to the server via the at least one network, a request to output still medical image data generated from moving medical image data, the still medical image data matching the at least one criterion specified by the second user input, the still medical image data being generated by applying the at least one image processing technique specified by the first user input.

16. The system of claim 15, wherein the server is configured to:
generate a still image from the moving image data; and
output the still medical image data based on the still image.

17. The system of claim 15, wherein the server is configured to:
use the at least one criteria specified by the second user input to identify the moving medical image data from which the still medical image data is generated.

18. The system of claim 15, wherein the server is configured to:
transmit, via the at least one network, the still medical image data to the terminal device.

19. The system of claim 15, wherein the at least one criterion includes at least one piece of information selected from a group consisting of: information identifying a patient, a user identifier, a date of imaging, and a time of imaging.

20. The system of claim 15, wherein:
the information identifying the at least one image processing technique comprises information identifying a version of an image processing algorithm performed to generate the still medical image data matching the at least one criterion; and
the server is configured to apply the identified version of the image processing algorithm to generate the still medical image data matching the at least one criterion.

21. A method implemented by a first apparatus comprising at least one processor, the method comprising acts of:
receiving first user input specifying at least one image processing technique for use in generating still medical image data from moving medical image data;
receiving second user input specifying at least one criterion for still medical image data generated from moving medical image data;
transmitting, to a second apparatus via at least one network, a request to transmit to the first apparatus still medical image data generated from moving medical image data, the still medical image data matching the at least one criterion specified by the second user input; and
outputting the still medical image data that is generated by applying the at least one image processing technique specified by the first user input.

22. A first apparatus comprising:
at least one computer-readable storage medium storing executable instructions; and
at least one processor programmed by the executable instructions to:
receive first user input specifying at least one image processing technique for use in generating still medical image data from moving medical image data;
receive second user input specifying at least one criterion for still medical image data generated from moving medical image data;
transmit, to a second apparatus via at least one network, a request to transmit still medical image data generated from moving medical image data, the still medical image data matching the at least one criterion specified by the second user input; and
outputting the still medical image data that is generated by applying the at least one image processing technique specified by the first user input.

* * * * *